United States Patent
Gregory

(10) Patent No.: US 6,522,910 B1
(45) Date of Patent: Feb. 18, 2003

(54) ELECTRICAL PROPERTY ENHANCED TOMOGRAPHY (EPET) APPARATUS AND METHOD

(75) Inventor: William D. Gregory, Charleston, WV (US)

(73) Assignee: WiSys Technology Foundation, Madison, WI (US)

( * ) Notice: Subject to any disclaimer, the term of this patent is extended or adjusted under 35 U.S.C. 154(b) by 0 days.

(21) Appl. No.: 09/508,250

(22) PCT Filed: Sep. 10, 1998

(86) PCT No.: PCT/US98/19223

§ 371 (c)(1),
(2), (4) Date: Mar. 8, 2000

(87) PCT Pub. No.: WO99/12470

PCT Pub. Date: Mar. 18, 1999

Related U.S. Application Data

(60) Provisional application No. 60/058,512, filed on Sep. 11, 1997.

(51) Int. Cl.⁷ .................................................. A61B 5/05
(52) U.S. Cl. ....................... 600/427; 600/428; 600/509; 600/547
(58) Field of Search ................................. 600/425, 427, 600/547, 508, 428, 509, 521, 529

(56) References Cited

PUBLICATIONS

Scott A. Hutchinson and Kwong T. Ng,"The Solution of 3–D Biomedical Electrostatic Problems on A Data Parallel Computer," Annual International Conference of the IEEE Engineering in Medicine and Biology Society, vol. 13, No. 2, 1991.

S. A. Hutchinson, S. Gao, L.Ai, K.T. Ng, O.C. Deale, P.T. Cahill, B.B. Lerman, "Three–Dimensional Modeling of Electrical Defibrillation on a Massively Parallel Computer," IEEE, Jul. 1982.

Hasan I. Saleheen, Paul D. Claessen, Rodney A. Hart and Kwong T. Ng, "Three–Dimensional Parallel Finite–Difference Bidomain Modeling of Cardiac Tissue," IEEE, Jun. 1994.

Michael E. Glidewell and Kwong T. Ng, "The Inclusion of Anatomical Contraints and Anisotropy in Three–Dimensional Electrical Impedance Tomography," 1994 IEEE.

Hasan I. Saleheen and Kwong T. Ng, "Parallel Finite Difference Solution of General Inhomogeneous Anisotropic Bio–Electrostatic Problems," IEEE, Jul. 1997.

Kwong T. Ng and Hasan I. Saleheen, "Three–Dimensional Bidomain Simulation of Electrical Propagation in Cardiac Tissue," IEEE, Jul. 1997.

Michael Glidewell and Kwong T. Ng, "Anatomically Constrained Electrical Impedance Tomography for Anisotropic Bodies via a Two–Step Approach," IEEE Transactions on Medical Imaging, vol. 14, No. 3, Sep. 1995.

*Primary Examiner*—Ruth S. Smith
(74) *Attorney, Agent, or Firm*—Quarles & Brady, LLP

(57) ABSTRACT

Enhanced information on the electrical properties of the subregions of a sample is generated by an enhanced tomography (EPET) apparatus connected to a tomographic device, wherein the EPET apparatus holds a voltage constant and measures the electrical current of the sample inserted within the EPET apparatus. A matching medium is applied to the sample such that when the sample is placed within an electromagnetic field generated by the EPET apparatus, the matching medium contacts the segmented sensor plates of the EPET apparatus and allows the detection of the net total charges Q on the surface of the sample. The EPET apparatus uses these net total charges Q in the calculation of the additional information on the electrical properties of the sample by using the scale factor method or the iterative correction method. The EPET apparatus and method has application in the medical imaging field, such as in the obtaining of enhanced dielectric constant and conductivity electrical properties values related to the imaging of the interior of the human body, e.g., in the determination of whether tissue is cancerous, dead or healthy.

45 Claims, 13 Drawing Sheets

FIG. 4
PRIOR ART
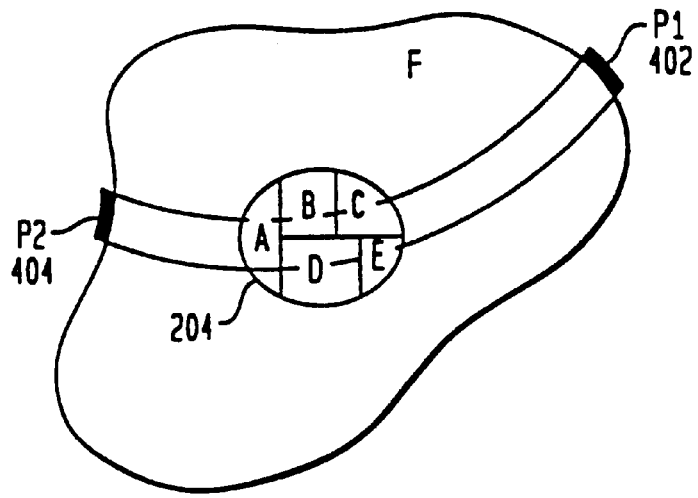
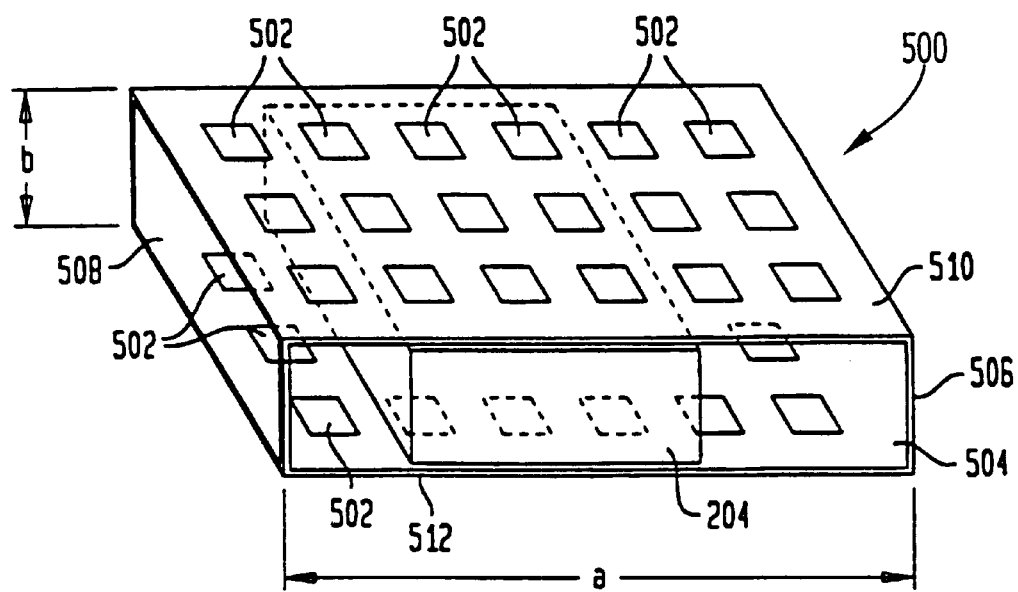
FIG. 5

ELECTRICAL PROPERTY ENHANCED TOMOGRAPHY (EPET) APPARATUS AND METHOD

This application claims the benefit of provisional application Ser. No. 60/058,512, filed Sep. 11, 1997.

BACKGROUND OF THE INVENTION

1. Technical Field

This invention relates to electrical imaging technology, and more specifically to an apparatus and method for enhancing the information obtained from conventional tomography, such as CAT and MRI scans, with accurate values of the electrical properties of the imaged object.

2. Background Art

Since Roentgen discovered the ability of x-rays to produce a shadowgram of the interior of a sample, there has been a substantial interest in scientific and engineering circles in technologies that allow the imaging of the interior of a sample using quantities measured exterior to the sample. While these technologies are often applied in industry and commerce generally, one of the most active areas for the use of imaging technologies is in the field of medicine. The original shadowgram x-rays were enhanced substantially with the discovery and perfection of computerized axial tomography, which allows the recovery of not just a shadowgram, but detailed information about the interior structure of a sample from x-ray intensities measured on the outside. A similar intense interest developed when nuclear magnetic resonance measurements were extended to map the interior of a sample in what is now commonly called Magnetic Resonance Imaging (MRI). Also, the use of ultrasound to explore the interior of samples has been a technology that has received substantial interest.

For all of these technologies (x-ray tomography, MRI, and ultrasound), an accurate picture in terms of spatial resolution is produced. However, information about the character of various objects located in the interior of a sample is often very limited. For example, x-ray tomography measures only the intensity of absorption at a single x-ray frequency and is generally simply proportional to the density of the material of the sample. The only improvements to conventional x-ray tomography have been to use x-rays at different frequencies which allow some information about both the density of objects in a sample (in terms of mass) as well as the electron density. Nonetheless, at best, only two new pieces of information are available from such measurements.

MRI is a modality that is sensitive to other parameters. Primarily, MRIs measure the number of protons (usually associated with hydrogen atoms) at any given point in a sample. Some extra information can be obtained with a great deal of analysis and care by measuring the decay time for certain magnetic resonance properties, but the sensitivity is such that perhaps three parameters can be measured using this technique.

A similar situation is obtained with ultrasound where there are yet some other complications due to the multiple reflections of the sound waves. While CAT scans and MRIs produce pictures that are somewhat familiar to even the untrained eye, ultrasound imaging requires a very skilled operator to perform the measurements and to interpret the results.

Because of the limitations of the existing imaging techniques, scientists and engineers have looked for other properties that might be exploited to produce an appropriate and improved image of the interior of a sample. One of these areas of exploration is in the use of electrical properties to produce such an improved image of the interior of a sample.

Therefore, there is a need for an apparatus and method for using the electrical properties of a sample to generate an improved image of the interior of the sample.

As a result of using the electrical properties of a sample to achieve an improved image of the sample's interior, conventional electrical property imaging techniques have developed which measure the electrical properties of different materials located within the sample. Such conventional imaging has shown that substantial variations within a sample from one type of material to another (e.g., in a biological sample such as a human being, from one type of tissue to another) is a function of measuring frequency. Despite this achievement, the originally hoped for capitalization on these techniques has yet to occur. Conventional electrical property imaging suffers from a lack of accuracy, due to a sensitivity to noise, and a somewhat fuzzy pictorial resolution.

Such conventional electrical property imaging techniques are often referred to as "impedance tomography." Early work in impedance tomography was performed at the University of Wisconsin resulting in rough and inaccurate images. Subsequent impedance imaging groups were started in England, and in the United States at Rennsalaer Polytechnic Institute and Dartmouth College.

All of the conventional electrical property imaging techniques are based on the premises that 1) electrodes, or sensors, should be attached directly to the sample to be measured (for medical applications, the sample is a human body), and 2) specific current should be injected into the sample and the subsequent voltages measured. Therefore, these conventional imaging techniques implement a "constant current/measured voltage" scheme. To date, the best result from such conventional techniques is approximately a ten to forty percent accuracy under typical measurement conditions.

In a departure from such conventional electrical property imaging techniques, the present inventor arranged sensors in an array outside the sample to be measured. See U.S. Pat. No. 4,493,039. Further, during imaging of a sample, the voltage was held constant while the current was measured. This method of using a "controlled voltage" was opposite of the current teachings in the relevant arts. Despite this new technique, it was impossible to generate accurate images of the interior of a sample because the sensors did not have any contact with the sample being measured. A further limitation to this controlled voltage method was the uniqueness of the imaging mathematics which was not fully realized at that time. Therefore, at the present time, there is a need for an apparatus and method that performs electrical property imaging using controlled voltage and in which sensors contact a sample being measured. There is still a further need for such an apparatus and method that takes full advantage of the uniqueness of the imaging mathematics associated with such controlled voltage imaging techniques.

Due to the high number and cost of existing imaging devices (CAT scans, MRIs, and ultrasounds), there is also a need for an apparatus and method that enhances the use of such existing imaging devices by adding information regarding the electrical properties of each region that is imaged in the interior of a sample.

DISCLOSURE OF INVENTION

The present invention solves the problems associated with conventional electrical imaging techniques by providing an Electrical Property Enhanced Tomography (EPET) apparatus and method that generates an accurate calculation of the electrical properties of a sample's interior subregions. The EPET apparatus is a plurality of sensors arrayed on a sample holder, in which a sample is place, that measure the net total charges Q on the surface of the sample holder.

Specifically, the EPET apparatus fixes the external voltages along points on the sample holder to generate an electromagnetic field within the sample holder. The EPET apparatus measures the electrical currents at a number of those fixed external voltage points on the sample holder, wherein the electrical currents are related to the electrical current that the electrical properties of the sample allow to pass according to the electromagnetic field.

The EPET apparatus of the present invention is connected to a tomographic device, e.g., a CAT scan or MRI device, for generating additional information on the electrical properties, i.e., the dielectric constant and conductivity, of a sample being measured. The EPET apparatus comprises one or more capacitive sensor arrays, each of which comprise a segmented capacitive sensor plate having a plurality of controller units connected thereto. Each controller unit controls the voltage and frequency in order to produce an electromagnetic field in the sample holder and then detects the net total charges Q on each segment of the capacitive sensor plate (which is related to the net total charges q within the sample when placed within the electromagnetic field of the sample holder). The EPET apparatus then uses the net total charges Q to calculate enhanced values of the electrical properties (the dielectric constant and conductivity) of the sample by using electromagnetic mathematical theory. In addition, a matching medium is applied to the sample during operation of the present invention such that the matching medium fills up the entire closed space and contacts the capacitive sensor arrays. In the preferred embodiment, the matching medium is chosen with dielectric constant and conductivity values that maximize the accuracy of the measurement.

An advantage of the present invention is that it enhances existing tomographic devices, e.g. CAT scans or MRIs. Therefore, current health care facilities can continue to use their existing devices, but with greater accuracy in imaging.

Another advantage of the present invention is that the processing is inherently parallel. Therefore, the imaging technique of an EPET apparatus and method is very fast as well as precise and robust.

BRIEF DESCRIPTION OF DRAWINGS

The present invention is described with reference to the accompanying drawings. In the drawings, like reference numbers indicate identical or functionally similar elements. Additionally, the left-most digit(s) of a reference number identifies the drawing in which the reference number first appears.

FIG. 4 is a planar view of a closed volume space being measured by a conventional electrical property imaging technique;

FIG. 5 is a three dimensional representation of a sample holder of the present invention;

BEST MODE FOR CARRYING OUT THE INVENTION

1. Host System of a Preferred Environment for the Present Invention

Figure 1:
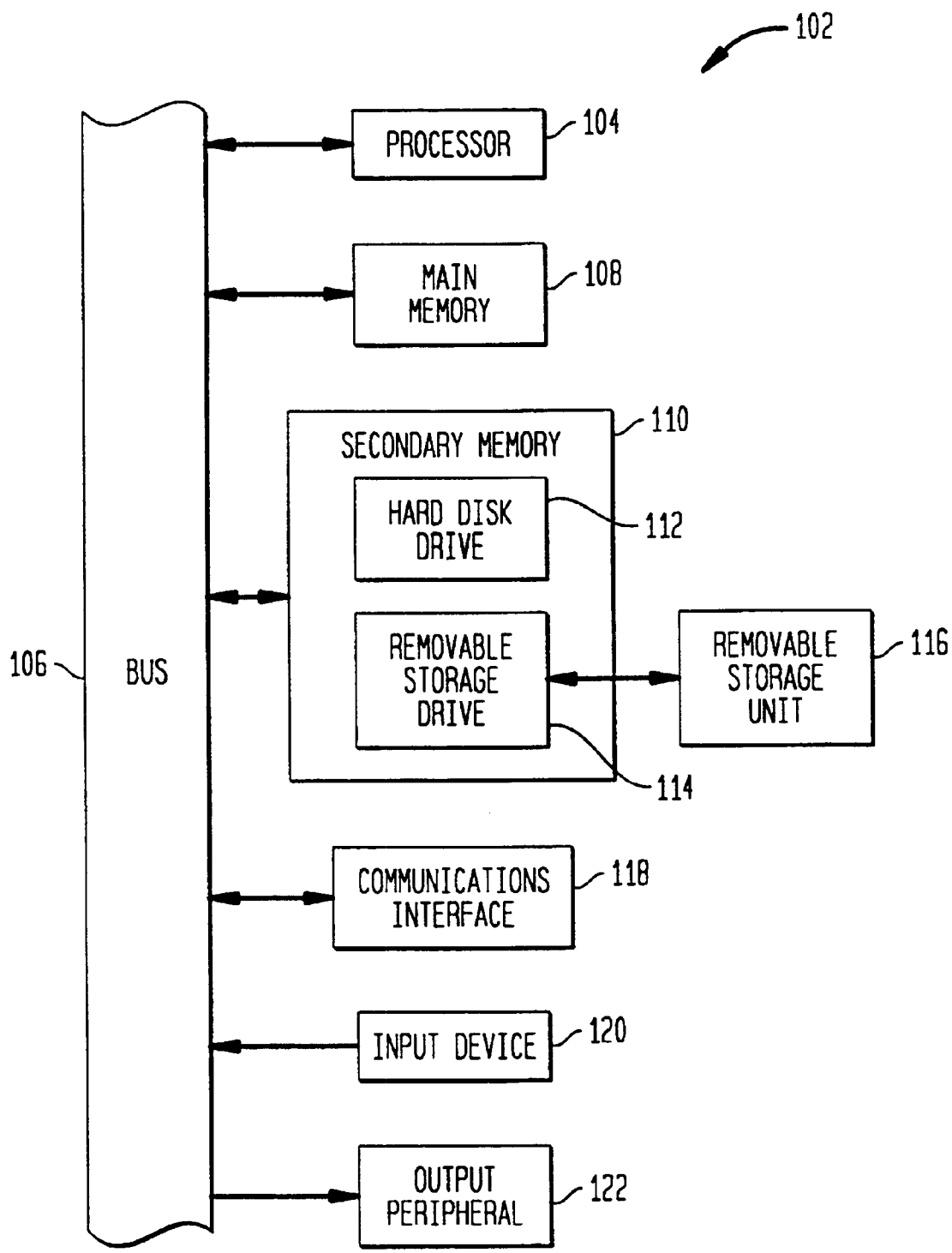
FIG. 1 is a block diagram showing an exemplary computer system useful for implementing the present invention.

The chosen embodiment of a component of the present invention is computer software executing within a computer system. FIG. 1 shows an exemplary computer system. The computer system 102 includes one or more processors, such as a processor 104. The processor 104 is connected to a communication bus 106.

The computer system 102 also includes a main memory 108, preferably random access memory (RAM), and a secondary memory 110. The secondary memory 110 includes, for example, a hard disk drive 112 and/or a removable storage drive 114, representing a floppy disk drive, a magnetic tape drive, a compact disk drive, a program cartridge and cartridge interface (such as that found in video game devices), a removable memory chip (such as EPROM, or PROM), etc. which is read by and written to by a removable storage unit 116. The removable storage unit 116, also called a program storage device or a computer program product, represents a floppy disk, magnetic tape, compact disk, etc. As will be appreciated, the removable storage unit 116 includes a computer usable storage medium having stored therein computer software and/or data. The removable storage drive 114 reads from and/or writes to a removable storage unit 116 in a well known manner.

The computer system 102 may also include other similar means for allowing computer programs or other instructions to be loaded. Such means can include, for example, a communications interface 118. Communications interface 118 allows software and data to be transferred between computer system 102 and external devices. Examples of communications interface 118 can include a modem, a network interface (such as an Ethernet card), a communications port, etc. Software and data transferred via communications interface 118 are in the form of signals which can be electronic, electromagnetic, optical or other signals capable of being received by communications interface 118.

In this document, the term "computer program product" is used to generally refer to removable storage unit 116, a hard disk installed in hard disk drive 112, and signals transferred via communications interface 118. These computer program products are means for providing software to a computer system 102.

In an embodiment where the invention is implemented using software, the software may be stored in main memory 108, or in a computer program product and loaded into computer system 102 using removable storage drive 114, hard disk drive 112, or communications interface 118. The software, when executed by the processor 104, causes the processor 104 to perform the functions of the invention as described herein.

In another embodiment, the invention is implemented primarily in hardware using, for example, a hardware state machine. Implementation of the hardware state machine so as to perform the functions described herein will be apparent to persons skilled in the relevant arts.

The preferred embodiment of the present invention is also directed to a computer system 102 including an output peripheral 122 and one or more input devices 120. The output peripheral 122 represents a computer screen or monitor on which a graphical user interface, including a window environment, may be displayed. The input devices 120 include, for example, a keyboard, a mouse, a light pen, a pressure-sensitive screen, etc., which provide a user with the capability of entering input to the computer system 102.

The present invention is described in terms of a computer system 102 having a single processor 104 for convenience purposes only. It would be readily apparent, however, to one skilled in the relevant arts to use a computer system 102 having multiple processors 104, e.g., an array processor, thereby executing the present invention in parallel. The preferred embodiment of the present invention is implemented in software, and more specifically, is written in the programming languages C and Interactive Data Language (IDL). The preferred embodiment is described in these terms for convenience purpose only. Other comparable computer systems 102, architectures, operating systems, and programming languages could alternatively be used.

2. Mathematical Discussion of the Present Invention

The following discussion describes the underlying mathematical theory of the controlled voltage electronic imaging technique of the present invention.

Figure 2:
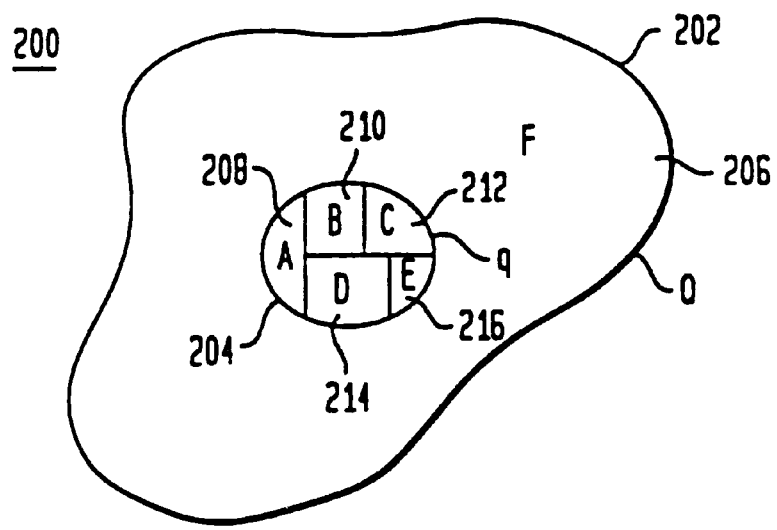
FIG. 2 is a planar view of a closed volume in space.

FIG. 2 is a planar view of a closed volume space 200 surrounded by a surface 202 that contains a sample 204 and an interior region F 206, such that region F 206 is the area between the sample 204 and the surface 202. The sample 204 comprises a plurality of connected subregions which for convenience are labeled: subregion A 208, subregion B 210, subregion C 212, subregion D 214, and subregion E 216, wherein each subregion 208–216 may be of a different material.

If an electromagentic field at some specified frequency (f) is applied to the sample 204 in the closed volume space 200, a net total charge is produced only where the electrical properties change, such as at the boundaries between each subregion 208–216 of the sample 204 where there is a dissimilarity in the dielectric constant and conductivity electrical properties of each subregion 208–216. These net total charges will in turn redistribute the net total charges on the surface of the closed volume space 200. The net total charge will exist only at places where there is a discontinuity in the electrical properties such as at the boundaries of the subregions 208–216 of the sample 204. It is assumed that there are both charges that are free to move individually (e.g., a free charge) as well as polarization charges located on the surface 202 of the closed volume space 200. The charges on the surface 202 are also net total (free plus polarization) charges wherein the net total charge on a point on the surface 202 is indicated with a capital "Q", while the net total charge on a point in the interior of the closed volume space 200 is indicated with a small "q." It is important to note that the measurement of the net total charge Q can involve either an actual measurement of the charge Q or the charge Q as derived from a small increment of the electrical current, I, which is the rate of change of the charge Q with time.

The net total charge at a point on the surface 202, Q, and the net total charge at a point in the interior, q, can be connected via electromagnetic theory. First, the fundamental theorem of electrostatics (the situation that occurs when the frequency of the electric field is "low", which is the situation for the current discussion) shows that an interior net total charge q and a net total charge on the surface 202 Q are uniquely related. The connection between these charges occur via a function called the Greens Function. However, in order for the Greens Function to be accurate, there must be an infinite number of terms in the series approximating this function. The present invention circumvents the need for such an infinite number of terms in the series and allows a connection to be made between an interior net total charge q and a net total charge Q with a limited, or finite, number of terms.

Once all interior net total charges q are known and all net total charge Q are either known or measured, the total electrical field interior to the closed volume space 200 can be then calculated. Based on this, it is then possible to compute the electrical properties of each subregion 208–216 contained within the closed volume space 200.

Figure 3:
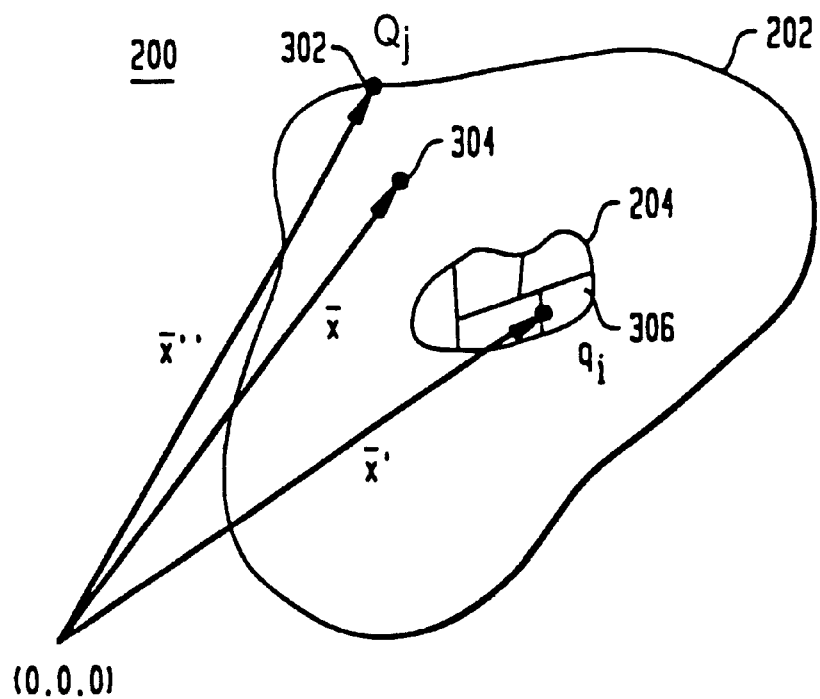
FIG. 3 is a planar view of a closed volume space showing the relationship between the measured exterior net total charges $Q_j$ and the interior net total charges $q_i$.

FIG. 3 is a planar view of the closed volume space 200 showing the relationship between the net total charge Q at a point on the surface 202 and a net total charge q at a point in the interior that are connected via The Greens Function. Specifically, The Greens Function connects a net total charge Q on the surface 202 at point j with an interior net total charge q at point i:$q_i \Leftrightarrow Q_j$. This relationship provides the desired information about the electrical properties of the interior subregions 208–216 of a sample 204. FIG. 3 illustrates the coordinate system and some of the relevant geometry used in this discussion.

The notation used in the coordinate system for the field point 304, the source point 306 and surface point 302 are $\overline{X}$, $\overline{X}$ prime ($\overline{X}'$), and $\overline{X}$ double prime ($\overline{X}''$) respectively. The present invention shows that by associating the net total charges q inside the sample 204 at the source point 306 with the net total charges Q at the surface point 302, an enhanced image of the interior of the sample 204 can be generated. Therefore, the position at which the electric field is measured is field point 304.

The controlled voltage technique of the present invention is opposite of the conventional electrical property imaging techniques. FIG. 4 is a planar view of a closed volume space 200 being measured by such conventional imaging techniques. Under such a method, charges are injected at known places, e.g., P1 402, on the surface 202 of the closed volume space 200 and extracted at known places, e.g., P2 404. The voltages on the surrounding sensors are then measured and the data is inverted.

One disadvantage with such conventional imaging techniques is that they require some assumption regarding the path of the charges through the interior of the closed volume space 200. Therefore, these techniques depend on a lumped circuit element approach (or equivalent) and on an estimate regarding the shape of the sample 204 being measured that is contained within the closed volume space 200. In contrast to these conventional techniques, the controlled voltage technique of the present invention allows one to fully describe the wave-like nature of the electric fields in the closed volume space 200 and the measuring volume and does not require any specific assumption ahead of time regarding the equivalent circuit character of the subregions 208–216 of the sample 204 being measured.

Applying the Maxwell Equations of electromagnetic theory to the problem as just described results in EQUATION 1A:

$$\nabla \cdot [(\sigma + j\omega\epsilon_0\epsilon_r)(-\nabla\Phi)] = 0$$

In addition, a standard result of electromagnetic theory is the connection between the potential, $\Phi$, and the total charge density, $\rho$, known as the Poisson Equation, EQUATION 1B:

$$\nabla^2 [\Phi] = \frac{\rho_{Total}}{\epsilon_0}$$

The EQUATIONS 1A and 1B show that for the electric field E and the scalar potential phi ($\phi$), the charges and charge densities that are important are that of the total charge, i.e., the free charge plus polarization charge.

In the present invention, the sources of the electric field are studied, which are the charges or the charge densities that produce the fields. In EQUATION 1B, the total net charge, i.e., the free charge plus the polarization charge, are important to the electric field E and the scalar potential phi ($\phi$).

One advantage of seeking the charges rather than going directly for the conductivity or dielectric constant is that one can see that the charges, which totally govern the electrical picture, only appear essentially at boundaries that are induced at discontinuities in this inhomogeneous medium. EQUATION 2 shows this since the gradient of the conductivity and the gradient of the dielectric constant contribute to the net total charge density. In fact, in a medium having both dielectric constant and conductivity properties, the build up of charges at a boundary arise not just from the gradient of the dielectric constant, which is commonly known from simple problems, but it also includes the gradient of the conductivity. Therefore, net total charge depends on the rapidity with which the conductivity and the dielectric constant change.

EQUATION 2:

$$\rho_{Total} = \frac{[\nabla\sigma + j\omega\nabla(\epsilon_0\epsilon_r)] \cdot \nabla\Phi}{\sigma + j\omega\epsilon_0\epsilon_r}$$

A standard theorem in electric magnetic theory is the Uniqueness Theorem. The Uniqueness Theorem states that if a potential or its normal derivative is known, then the potential at a field point 304 can be uniquely determined. It is important to note that both the potential and the normal derivative of the charge need not be known. In fact, the problem would be over determined if both were known. While it is possible to define the problem with the potential known on some set portion of the bounding surface and the normal derivative on other portions, EQUATION 3 considers the simple case where the potential on the surface 202 is known. EQUATION 3 is the solution to Poisson's Equation (EQUATION 2) using the Green's Function.

EQUATION 3:

$$\Phi(\bar{x}) = \frac{1}{4\pi\epsilon_0} \int \rho_{Total}(\bar{x}') \times G_D(\bar{x}, \bar{x}') d\tau - \frac{1}{4\pi} \oint_S \Phi(\bar{x}'') \frac{\partial G_D(\bar{x}, \bar{x}'')}{\partial n''} dS$$

EQUATION 3 is the potential at the field point 304 as determined by the net total charge q on the interior and the potential on the surface 202, exactly as the Uniqueness Theorem predicts. The solution is obtained in the terms of a geometrical function, the Green's Function, which is a standard treatment. When a sample 204 is present, both the volume integral over the net total charge q density and the surface integral over the surface 204 are present. If the same potential distribution on the surface is considered but with no sample present, then the charge density goes to zero but the surface integral remains the same. The surface term (the second integral) is unchanged by inserting the sample 204 because the voltage is set to pre-determined values on the surface 202 and kept at those values before and after inserting the sample 204. Because of this, when the two terms are subtracted, the remaining expression involves only the Green's Function (which is a known quantity for a given shape of the array of measuring sensors) and the charge density. Therefore, it is convenient to use the difference in the potential between the case when a sample 204 is inserted and when a sample 204 is not inserted between the sensors.

This difference can be related to the charges at the surface 202 by taking the normal derivative. EQUATION 4 then shows that those charges at the surface 202 labeled by the index "j" will be related to the charges on the interior labeled by the index "i" by a matrix element involving both "j" and "i" which is simply the normal derivative of the Green's Function.

EQUATION 4:

$$\delta Q_j = Q(j)_{Total}^{Full} - Q(j)_{Total}^{Empt} = \Sigma q_{Total} \cdot \frac{\partial G_D(j, i)}{\partial n''_j}$$

EQUATION 5 shows that this series of equations in "j" can be written down and grouped together in matrix formation involving a charge on the surface 202 as a vector with each term of the vector one of the net total charges. For the charges on the surface 202, a capital "Q" is used and they are related to a similar vector for which each term is one of the net total charges on the interior using the small "q."

EQUATION 5:

$$\overline{\delta Q} = \overline{\delta q} \cdot \overline{\frac{\partial G_D}{\partial n''}}$$

The series of equations is inverted to give the charges on the interior, "q", provided that the matrix itself has an inverse. More specifically, the Green's Function derivative matrix is multiplied by its inverse, resulting in a unitary matrix if an inverse exists. See EQUATION 6.

EQUATION 6:

$$\overline{\frac{\partial G_D}{\partial n''}} \cdot \left(\overline{\frac{\partial G_D}{\partial n''}}\right)^{-1} = I = \begin{pmatrix} 1 & 0 & . & . & 0 \\ 0 & 1 & 0 & . & . \\ . & 0 & 1 & . & . \\ . & . & . & 1 & 0 \\ 0 & . & . & 0 & 1 \end{pmatrix}$$

FIG. 5 is a three dimensional representation of a sample holder 500 of the present invention having a sample 204 contained therein. A plurality of sensors 502 are arrayed on each side of the sample holder 500 in a matrix configuration. For convenience purpose only, a two dimensional cross-section of the closed volume space 200 is graphically represented as the entire space within the sample holder 500 having a height b, represented by coordinates (0,b), and a length a, represented by coordinates (a,0). Therefore, the surface 202 of the closed volume space 200 becomes the surface of the sample holder 500. Also for convenience, only several of the sensors 502 are labeled on FIG. 5, but the discuss herein relates equally to all sensors 502.

The preferred embodiment of the present invention is described in terms of a rectangular sample holder 500 for convenience purposes only. It would be readily apparent to one of ordinary skill in the art to use a sample holder 500 of a different geometric cross-sectional shape. When such a new shape is used, the sine function used to generate the Fourier transform values would be replaced by a function chosen from an appropriate orthonormal set of functions particular to the new shape of the sample holder 500.

A sample 204 is placed inside the sample holder 500 with a matching medium 504 that matches the impedance between the sample 204 and the sensors 502. More specifically, the matching medium 504 matches the average impedance of the entire sample 204. The sensors 502 are segmented metal strips on each side (the sides 506, 508, top 510 and bottom 512) of the sample holder 500. Each sensor 502 serves the dual purpose of providing a controlled voltage to the sample 204, thereby generating the electromagnetic field, and of measuring the electrical current, or net total charge Q, over a fixed interval.

There are four basic orientations of the sample 502 in the rectangular space 500: two in the vertical direction and two in the horizontal direction. By keeping a constant potential on the top 510 of the rectangular space 500, a different constant potential on the bottom 512 of the rectangular space 500, and a gradient that spans the two potentials on the sides 506, 508, an electric field is produced in the vertical direction. Similarly, by putting a constant potential on the one side 506 of the rectangular space 500, a different constant potential on the other side 508 of the rectangular space 500, and a gradient between these two potentials on the top 510 and bottom 512, an electric field is produced in the horizontal direction. For these conditions we see that there are four combinations of sample 204 direction and electrical field direction. See TABLE 1.

TABLE 1

| Orientation (OR) | Sample Direction (S) | Electrical Field Direction (E) |
|---|---|---|
| 1 | ↑S | ↑E |
| 2 | ↑S | →E |
| 3 | →S | ↑E |
| 4 | →S | →E |

Sample 204 orientations can be changed by rotating the plates of the sample holder 500 or by rotating the sample 204 itself. Such rotation can be achieved by hand or by an automated means.

From these four orientations, fifteen combinations can be made by either using a specific orientation individually or by combining together the first and second; the first and third; the first and fourth; the second and third; the second and fourth; the third and fourth; the first, second, and third; the first, second and fourth; the first, third and fourth; the second, third, and fourth; the first, second, third, and fourth. Therefore, there are fifteen possible combinations of field direction and sample orientation with which to work. See TABLE 2.

TABLE 2

| Combination | Orientations |
|---|---|
| 1 | 1 |
| 2 | 2 |
| 3 | 3 |
| 4 | 4 |
| 5 | 1,2 |
| 6 | 1,3 |
| 7 | 1,4 |
| 8 | 2,3 |
| 9 | 2,4 |
| 10 | 3,4 |
| 11 | 1,2,3 |
| 12 | 1,2,4 |
| 13 | 1,3,4 |
| 14 | 2,3,4 |
| 15 | 1,2,3,4 |

EQUATION 7 shows how to get rid of the double sum that is going to appear in the expression for the net total charge Q on the surface 202 of a sample 204. Once the Green's Function is expanded in a complete set of orthogonal functions (which is just the sine function), the result is a sum over the parameter "L" which appears inside the sine function in EQUATION 7 and also a sum over the charges which appears in EQUATION 4. By multiplying by the appropriate sine function for given value "L", and summing up over the top side 510 or the bottom side 512, the sum over "L" can be eliminated, thereby having just one term remain. This result occurs because of the orthogonality property of sine and cosine functions. The accuracy can be further improved by subtracting the results from the top 510 and bottom 512, resulting in the equation for a given value of "L" for the Fourier Transform (the sine transform) as shown in EQUATION 8.

EQUATION 7:

$$\int_0^a [\delta Q_{Top}(j) - \delta Q_{Bottom}(j)] \cdot \sin\left(\frac{1 \cdot \pi \cdot x''}{a}\right) dx'' = FT(l)$$

EQUATION 8:

$$FT(l) = \sum_i \frac{q_i \cdot \sin\left(\frac{1 \cdot \pi \cdot x_i'}{a}\right) \cdot \sinh\left(\frac{1 \cdot \pi \cdot \left(\frac{b}{2} - y_i'\right)}{a}\right)}{\sinh\left(\frac{1 \cdot \pi \cdot b}{2a}\right)}$$

The procedure now is relatively simple. For as many values as "L" as desired, one equation can be produced each of which involves the sum over the charges labeled by "i," the matrix elements of which are shown in EQUATION 8. This set of equations becomes somewhat better conditioned, i.e., one equation differs more from the other, if the length of the small side "b" is small compared to two times the length of the long side "a." When this condition is satisfied, the denominator of the matrix element is small, making the whole matrix element large and meaning in turn that for different values of the matrix element, i.e., different values of the "x" and "y" position, different values result. Note also that the extra factor of two appears in the front of the "a" because of taking the difference in the charges between the top 510 and bottom 512 plate. Nonetheless, highly accurate results can be obtained for a=b.

As a result of the foregoing, there are two different ways to use this set of equations to invert and gain information about the electrical properties on the subregions 208–216 inside a sample 204. In both cases, the calculated net total charges q on the interior of a sample 204 are only used indirectly. A certain distribution for the electrical properties is assumed, a first guess, and then two different techniques are used to determine whether that first guess is close to the experimental value or not.

The first way to generate information about the electrical properties on the subregions 208–216 inside a sample 204 is shown in EQUATION 9 wherein the Fourier transforms are grouped as a column vector and are related to the net total charges q in the geometrical matrix by multiplying the charges by another vector called the scale factor "S". Each term in the scale factor is simply a weighting factor to be multiplied with each group of charges that have a common property. For example, for a typical human subject, the charges are grouped according to the type of boundary, e.g., all the net total charges q between skin and muscle have a certain scale factor whereas there is another scale factor for all the charges, or boundaries, between fat and skin. Such a grouping is logical because it is known that the discontinuity in the dielectric properties at such a boundary will generally produce approximately the same net charges, at least in a zero order approximation. The result of this type of grouping is then to produce a matrix equation which will connect the Fourier transforms for different values of the Fourier index L and sample orientations to a scaling factor for each group of boundary types. If in fact the correct value of the dielectric parameters have been guessed, then all of the elements of the scale factor vector will be one.

EQUATION 9:

$$\overline{FT} = \overline{\overline{q_{\text{Geometry}}}} \cdot \overline{S}$$

$$\overline{FT} \leftrightarrow \overline{S}$$

On the left hand side, the Fourier transform for an assumed distribution of electrical properties is calculated using methods discussed below. On the right hand side, the values for another assumed distribution of electrical properties are calculated. The values for the scale factors in each case are determined by comparing the theoretical value on the right to the experimental value on the left. This is accomplished by inverting the equation which results in a whole series of scale factors which are then compared to a whole series of Fourier transforms coming from so-called "true" material values. This results in a large calculation but it can be performed offline before the actual measurements take place. The offline calculation allows the generation of a set of look up tables, or the application of a neural net analysis. Using either the tables or the neural net equation, the scale factors resulting from the inversion of the equation in the actual experiment can be connected to the corresponding dielectric constant or conductivity values.

This scale factor method has been tested for data grouped according to sample boundary types and appears to be a very good method for getting within a reasonable value of the dielectric constant electrical properties thereof. Using approximately 6,000 possible combinations, a neural net was set up that was trained in about 100,000 passes and was able to connect the dielectric properties or predict the dielectric properties for a five parameter dielectric having only real values (no conductivity) to within one percent. A similar result was obtained with a look up table for the same data. In an alternative embodiment, other grouping types besides boundary types could be used. For example, by calculating the change in the net total charges for a given change in the dielectric values, the data can be grouped according to the assumed dielectric subregions of a sample 204.

Therefore, the scale factor method appears to be a good technique for getting a crude idea of what the electrical properties are. However, the real accuracy is achieved from the second technique called iterative correction method shown in EQUATION 10.

EQUATION 10:

$$\overline{FT}_{\text{Exp}} - \overline{FT}_{\text{Trial}} = \overline{\frac{\partial FT}{\partial \varepsilon}} \cdot \partial \varepsilon$$

In this method, the Fourier transform that is calculated by theory for a given assumption of the dielectric constant values and conductivity is subtracted from the value measured experimentally. The change in the Fourier transform is then computed using the chain rule of calculus and can then be related to the actual difference using the matrix so generated. The net result is then inverted to produce a value for the increment in dielectric constant and conductivity values necessary to produce the measured difference in Fourier transform values. This change in the dielectric constant and conductivity values can then be added back and the new change in the Fourier transform is calculated.

More specifically, EQUATION 10 shows that the difference between the experimental Fourier transform and a trial value of the Fourier transform can be obtained by using the chain rule of calculus and a sum of derivatives over each of the parameters affecting the Fourier transform, which are essentially each of the dielectric or conductivity values. In this context, the vector for the dielectric constant is really a vector that has as its real part the conductivity and as its imaginary part the dielectric constant for each of the subregions 208–216 of the sample 204.

To perform either of the calculations of EQUATION 9 or EQUATION 10, there must be a method for computing the net total charges Q on the surface 202 of a sample 204 and the net total charges q on the interior thereof. EQUATION 11 illustrates such a method, called the finite difference solution.

EQUATION 11:

$$\oint_{\text{about}(s,t)} [(\sigma + j\omega\varepsilon_0\varepsilon_r) \cdot (\nabla\Phi)]dS = 0$$

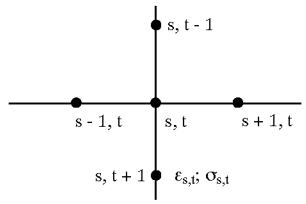

EQUATION 11 states that the divergence of the quantity in the brackets is zero, which means that by using Gauss' law, the surface interval of that quantity over a surface bounding a point of interest must also be zero. Therefore, this gives a condition on the electrostatic potential for known values of the dielectric constant and conductivity that can be solved in an iterative fashion.

The following software, written in the Interactive Data Language, illustrates the calculations of the finite difference solution of EQUATION 11:

e5=(e(1:NX-2,1:NY-2)+e(0:NX-3,1:NY-2)+$
    e(0:NX-3,0:NY-3)+e(1:NX-2,0:NY-3))*2
e1=e(1:NX-2,0:NY-3)+e(1:NX-2,1:NY-2)
e2=e(1:NX-2,0:NY-3)+e(0:NX-3,0:NY-3)
e3=e(0:NX-3,1:NY-2)+e(0:NX-3,0:NY-3)
e4=e(0:NX-3,1:NY-2)+e(1:NX-2,1:NY-2)
p(1:NX-2,1:NY-2)=( (e1*pold(2:NX-1,1:NY-2)+$
    e2*pold(1:NX-2,0:NY-3)+$
    e3*pold(0:NX-3,1:NY-2)+$
    e4*pold(1:NX-2,2:NY-1) )/$
    e5)
    p=p+Alpha*(p-pold)

In IDL, it is possible to assign values to quantities over an entire range (essentially a parallel operation). Using this parallel methodology, the technique to set up the conditions of EQUATION 11, which are the conditions shown in the above code, and produce a new potential "p" by reassignment of the potentials to each point based on the averaging applied by EQUATION 11. It is important to have an acceleration factor Alpha which accelerates the convergent of the iteration. In the present invention, the Alpha value has been calculated for totally real potentials, however, it appears to work well when the appropriate Alpha values are applied to complex potentials. The Alpha value is essentially a function of the shape of the grid work and the number of points in the grid work.

The finite difference solution proceeds by demanding that the finite difference code be satisfied at every point, only stopping when the potential before (p) and potential after (p-pold) is less than a certain error for any point in the subregion 208–216. In the preferred embodiment, both the real and imaginary parts have been solved wherein both parts do not have an error greater than one part in one hundred million. In many cases, this condition can be relaxed to one part per ten million. In any case, this is not a required experimental accuracy, but merely a calculational limit.

The preferred embodiment of the present invention uses the iterative correction method and has been tested using CAT scans of the human body. Such tests have produced an error that is much less than one percent for errors of one percent in the charge measurements on the surface of a sample. This is a great improvement in the accuracy of conventional electrical imaging techniques which produce a ten to forty percent accuracy for approximately the same accuracy of the measured parameters.

3. EPET Apparatus

Figure 6:
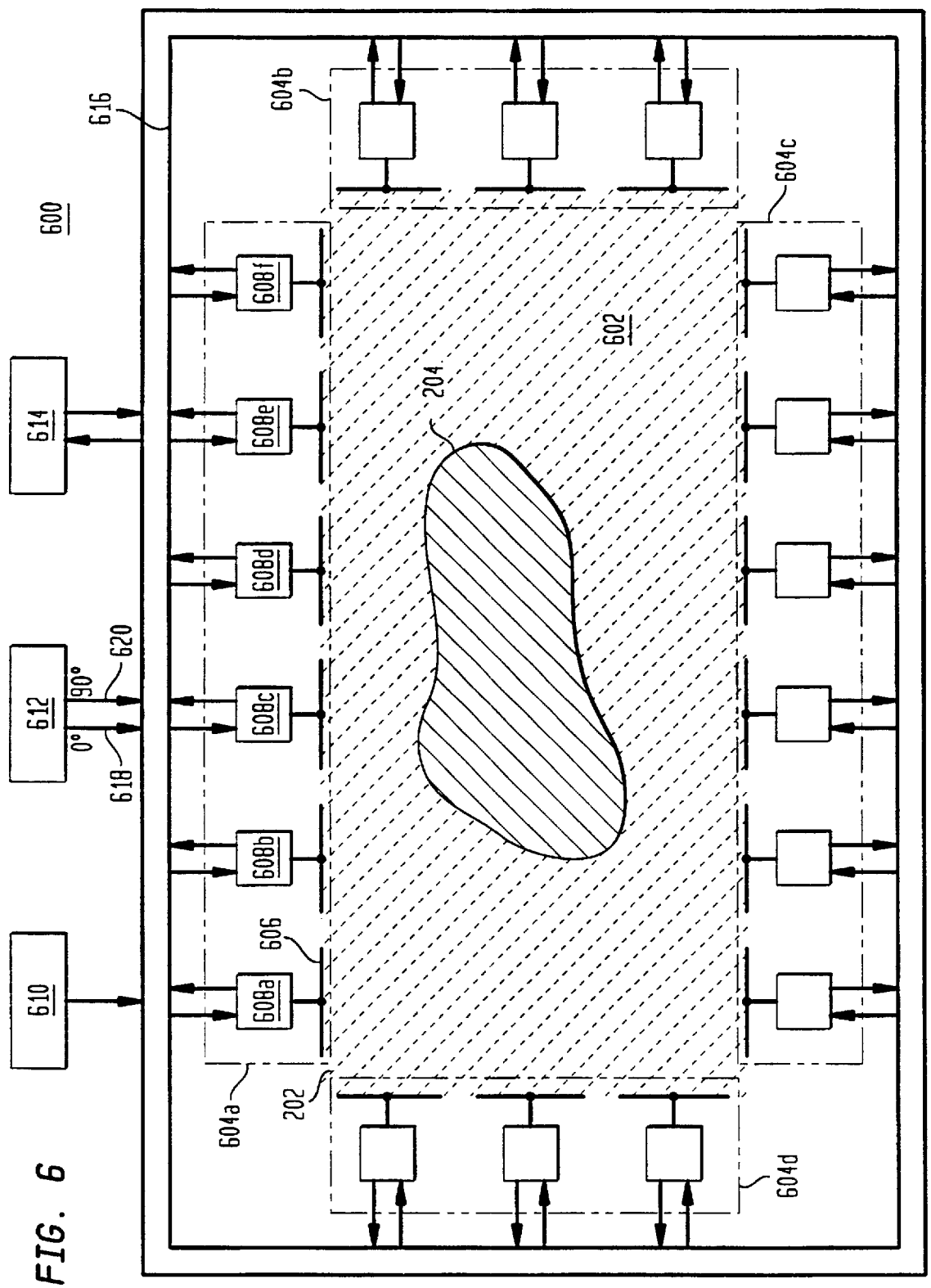
FIG. 6 is a block diagram showing an EPET apparatus of the present invention.

FIG. 6 is a block diagram showing an EPET apparatus 600 of the present invention with a sample 204 contained therein for measuring. In the preferred embodiment, the EPET apparatus 600 comprises a capacitive sensor array 604a–d on each side of the sample 204 for detecting the net total charges Q at each point on the surface 202 of the sample 204. Specifically, there is a top array 604a, right side array 604b, bottom array 604c, and left side array 604d, which collectively form a sample holder 500. Therefore, the surface 202 of the sample 204 is the surface of the capacitive sensor arrays 604a–d (the sample holder 500). The preferred embodiment is described in terms of these four capacitive sensor arrays 604a–d for convenience purpose only. When the sample 204 is thick, the preferred embodiment comprises at least two capacitive sensor arrays 604a,c. However, it would be readily apparent to one of ordinary skill in the art to use an apparatus and method of the present invention using one or more such capacitive sensor arrays 604 for detecting the net total charges Q at the surface 202 of a sample 204.

In operation, which is described in greater detail below, a sample 204 is placed between the capacitive sensor arrays 604a–d with two sides of the sample 204 being reasonably close to the capacitive sensor arrays 604a–d and with a matching medium 602 applied on the sample 204 as a buffer between the sample 204 and the capacitive sensor arrays 604a–d. Enough matching medium 602 is used to fill up the remainder of the sample holder 500 surrounding the sample 204. This preferred embodiment of matching medium 602 minimizes error in reading the net total charges of the sample 204.

A matching medium 602 is used to produce appropriate net total charges Q at the segmented sensor plate 606 (which is equal to the surface 202 of the sample 204). Specifically, a matching medium 602 is chosen for a sample 204 such that the medium 602 optimizes the accuracy of the resulting dielectric constant and conductivity of each subregion 208–216 of the sample 204.

Each capacitive sensor array 604a–d comprises an identical structure. For the purpose of convenience only, one capacitive sensor array 604a is described, however, the description is equally applicable to the other capacitive sensor arrays 604b–d of the present invention. A capacitive sensor array 604a comprises a segmented sensor plate 606 having a plurality of controller units 608a–f applied thereon and arranged in a matrix format. Each controller unit 608a–f applies the desired voltage to the sample 204 at a desired frequency, thereby generating an electromagnetic field, as well as detects the net total charge Q at the segmented sensor plate 606. A controller unit 608a is described below in greater detail.

In the preferred embodiment, the length of the top and bottom capacitive sensor arrays 604a, c is denoted by array length "a", and the space between these capacitive sensor arrays 604a, c (the left and right capacitive sensor arrays 604b,d) is denoted by array width "b". It is important to note that the value of the net total charge read from a capacitive sensor array 604a–d drops off as the segmented sensor plate 606 gets longer and therefore further away from the sample 204 being measured. In the preferred embodiment, the ratio of the array length "a" to the array width "b" should be such that array length "a" is much greater than array length "b". Specifically, the ratio (array length "a"/array width "b") equals approximately three to five which yields more accuracy than other ratios. Typically, for the ratio (array width "b"/2) multiplied by the array length "a") to equal 1/10, then for low values of the index i, the size of the matrix elements and the derivative of the matrix elements with distance (which measures the ability to distinguish one point in the picture from another) will be very substantial. This observation is directly related to the ability of the EPET apparatus 600 of the present invention to generate a noise insensitive, but sample 202 sensitive, image. In an alternative embodiment, a 1-to-1 ratio is sufficient, but results in slightly lower accuracy.

A power supply 610, frequency source 612, and a computer system 614 are connected to the capacitive sensor arrays 604a–d by a bus 616. The power supply 610 provides the necessary DC power for the components of the sensor array 604 and the frequency source 612 provides the necessary alternating voltage to the capacitive sensor arrays 604a–d for measuring the sample 204 contained therein. In the preferred embodiment, the frequency source 612 provides both a zero degree component 618 (in-phase) and a ninety degree component 620 (out-of-phase) of the alternating voltage being output from the controller units 608a. Further, the frequency can be changed from time to time so that the EPET apparatus 600 can make a multiple frequency measurement as needed. The computer system 614 controls the components of the EPET apparatus 600 and performs the calculations needed to generate the dielectric constant and conductivity electrical properties of the sample 204. In addition, although not shown on the figures, the EPET apparatus 600 is connected to a tomographic device via the computer system 614. It would be readily apparent to one of ordinary skill in the relevant art to install the EPET apparatus 600 of the present invention with a tomographic device.

Figure 7:
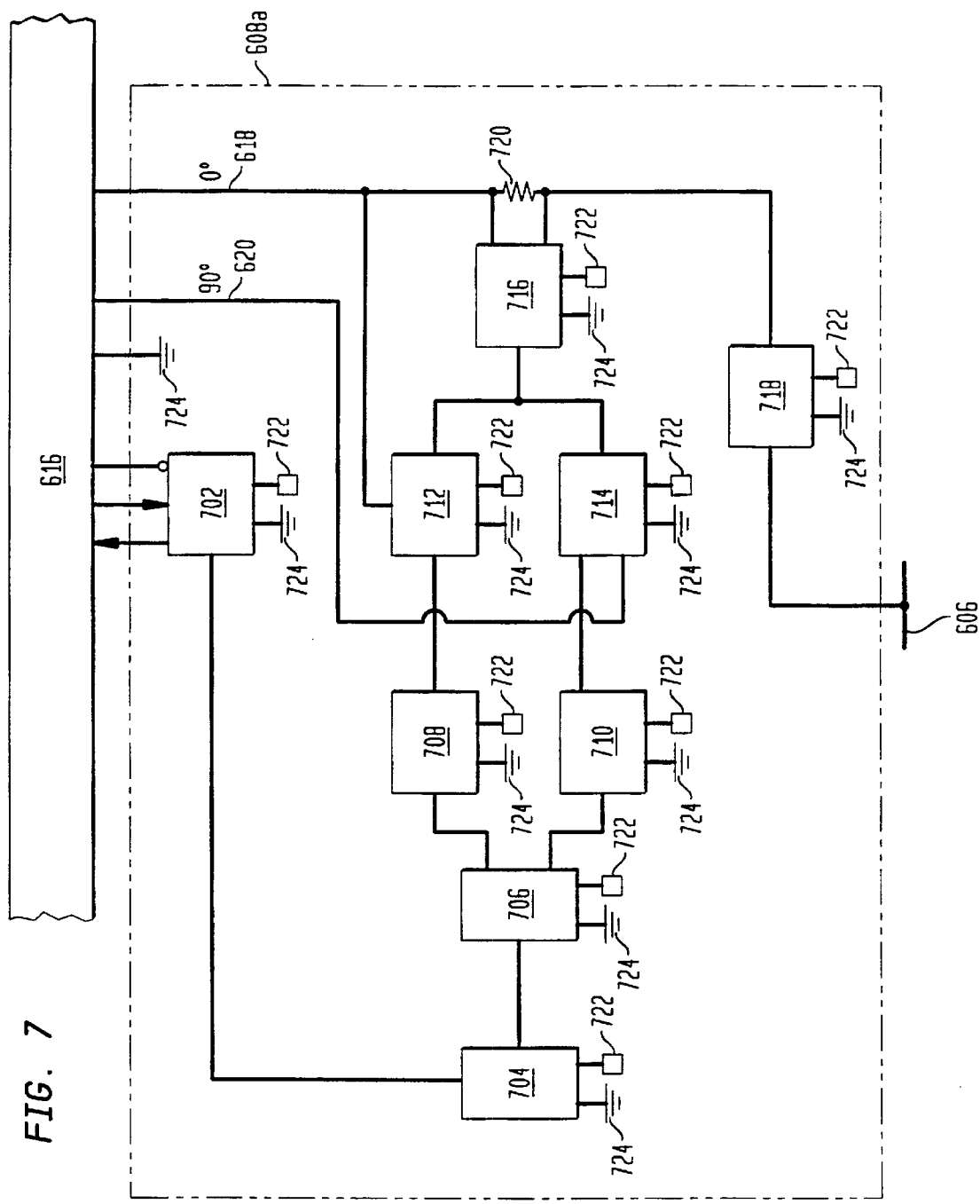
FIG. 7 is a block diagram showing a controller unit of the EPET apparatus of the present invention.
Figure 8:
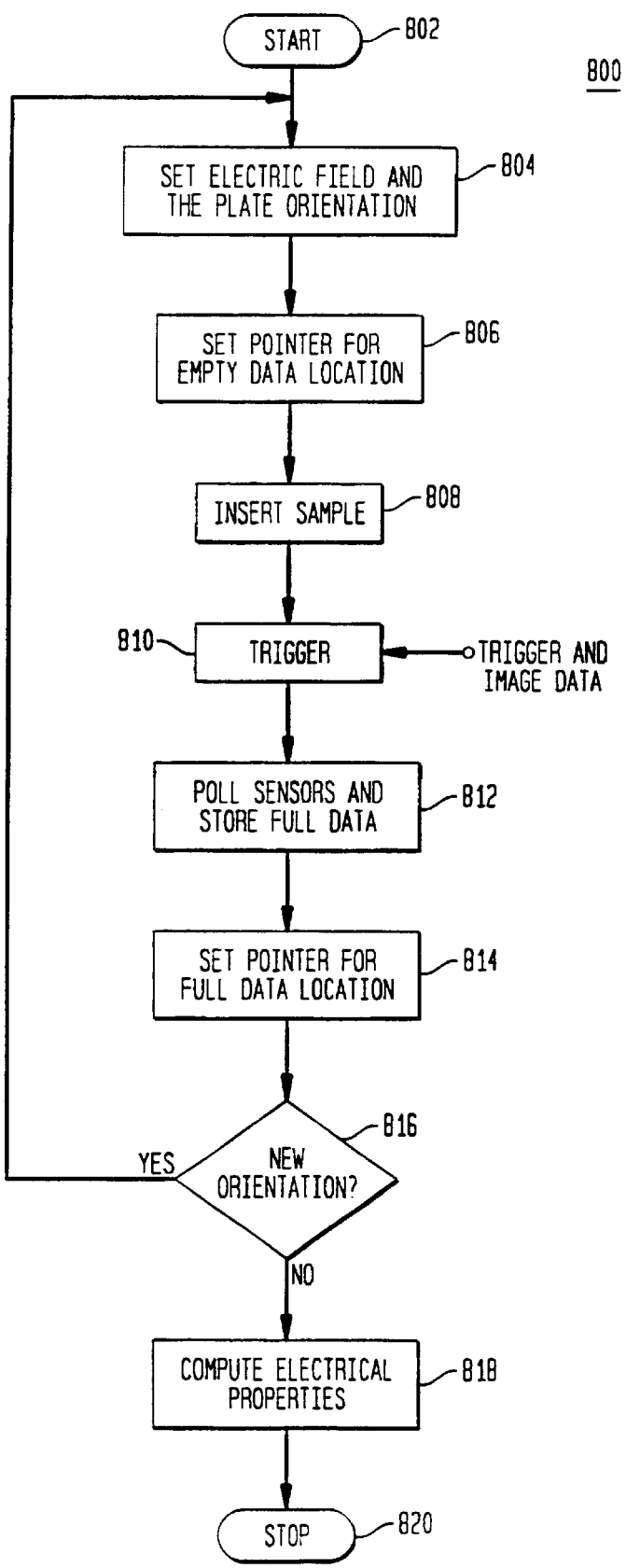
FIG. 8 is a control flow diagram showing the operation and method of the EPET apparatus.

FIG. 7 is a block diagram illustrating the structure of a controller unit 608a of a capacitive sensor array 604a of the present invention. Each controller unit 608a comprises an identical structure. For convenience purpose only, one controller unit 608a is described, however, the description is equally applicable to the other controller units 608b–f of the present invention. The controller unit 608a of the present invention is described in these structural terms for convenience purpose only. It would be readily apparent to one of ordinary skill in the relevant arts to use a controller unit 608a having a different structural design.

In the preferred embodiment, a controller unit 608a comprises multiple components, including but not limited to, a local controller 702, an A/D converter 704, a multiplexer 706, a first Sample/Hold (S/H) component 708, a second S/H component 710, an out-of-phase phase (90 degree frequency) sensitive detector 712, an in-phase phase (0 degree frequency) sensitive detector 714, an auto-gain controller 716, a segment voltage controller 718, and a pure resistor 724. These components communicate via a local digital bus 722. Further, these components communicate with the other parts of the EPET apparatus 600 via the bus 616. More specifically, the controller unit 608a transmits and receives data to/from the computer system 614, receives power 724 from the power supply 610, and receives in-phase and out-of-phase alternating voltage from the frequency source 612 over the bus 616.

In operation, the computer system 614 commands the segment voltage controller 718 of the controller unit 608a to set a given alternating voltage at a specified frequency. The pure resistor 724 is used to create a voltage that is an accurate measure of the magnitude and phase of the electrical current. Also, the computer system 614 engages the auto-gain controller 716 to maximize the voltage on pure resistor 724 reflective of the electrical current, or charge, inputted to the phase sensitive detectors 712, 714. Next, the computer system 614 commands the in-phase phase sensor detector 712 and the out-of-phase phase sensor detector 714 to read the net total charges Q on the segmented sensor plate 606. The controller unit 606 transmits these net total charges Q to the computer system 614 via the first S/H 708, the second S/H 710, the multiplexer 706, the A/D converter 704 and the local controller 702. These components operate using conventional methods. It would be readily apparent to one of ordinary skill in the relevant arts to convert the analog format of the net total charges Q to digital values and then transmit these digitized net total charges Q to the local controller 702 and the computer system 614 for further processing.

4. EPET Method and Control Flow

In operation, the EPET apparatus 600 will be incorporated into a standard tomographic device, e.g., the x-ray tubes and detectors of a computer axial tomography (CAT) device. This combination allows the standard tomographic device to determine the initial position of a sample 204, and the subregions 208–216 thereof, very quickly while having the EPET apparatus 600 simultaneously read the net total charges Q on the segmented sensor plate 606, and calculate the enhanced dielectric constant and conductivity electrical properties of the subregions 208–216 of the sample 204.

FIGS. 8–11 are block diagrams illustrating the operational control flow of the EPET apparatus 600. Referring to these figures, the method of using the EPET apparatus 600 with a standard tomographic device 620 is described below in detail.

Control starts at step 802 at which the computer system 614 inputs initial start-up data, including but not limited to, a source indicator for empty data values, the orientation of the sample 204 in the sample holder 500, and first guess values for the electrical properties values. At this step, the computer system 614 also generates an electromagnetic field within the sample holder 500 of the EPET apparatus 600 according to a predetermined voltage. After start-up, processing proceeds to step 804. In step 804, the computer system 614 of the EPET apparatus 600 sets the electromagnetic field according to a given voltage and frequency of each controller unit 606 and sets the orientation of the sample 204. Processing continues to step 806. In step 806, the computer system 614 sets the address pointer for the empty data values. The empty data values are the net total charges Q when a sample 204 is not in the EPET apparatus 600; that is, only the matching medium 602 is present in the sample holder 500. Step 806 is described in greater detail below. Processing then continues to step 808.

In step 808, a sample 204 is placed between the capacitive sensor arrays 604a–d, or the sample holder, of the EPET apparatus 600. Proceeding to step 810, the EPET apparatus 600 waits for a trigger from the tomographic device to which it is connected. By using this triggering mechanism, the EPET sensor measurements of the net total charge Q and the CAT scan image data are insured to occur at precisely the same time, for the same condition of the sample 204. The tomographic device makes a preliminary determination of the shape and position of all the subregions 208–216 of the sample 204 and transmits this imaging data to the computer system 614 of the EPET apparatus 600, thereby triggering the EPET apparatus 600 to poll its phase sensitive detectors 712, 714 to receive the net total charge Q on the surface 202 of the sample 204. In an alternative embodiment, triggering can be tied to a convenient time for optimum information about the sample 204, such as at specifically monitored portions of the cardiac or pulmonary cycle of a human subject when noise is minimized. In such a case, an external device, e.g., electrocardio machine or respiratory sensing device, generates a trigger signal which then triggers the EPET apparatus 600 and the tomographic device simultaneously. Upon receiving the trigger from the tomographic device, the EPET apparatus 600 continues to step 812.

In step 812, the computer system 614 commands the controller units 606a–f to poll their sensors, the phase sensitive detectors 712, 714, and measure the net total charge Q on the segmented sensor plate 606. This represents the full data values which are the net total charges Q when the sample 204 is located within the sample holder 500 of the EPET apparatus 600. This polling of the sensors is performed in parallel so that the time averaging for any one measurement is the same as the time averaging for all measurements. Once the data is received, the EPET apparatus 600 continues to step 814. In step 814, the computer system 614 sets a data pointer to the full data it just read from the polling of the sensors and proceeds to step 816.

In step 816, the computer system 614 determines whether there is a new orientation for the sample 204 or the electric field as it is contained within the sample holder 500 of the EPET apparatus 600. If a new orientation exists, the computer system 614 returns to step 804 to restart its processing of the sample 204. If a new orientation does not exist, the computer system 614 continues to step 818. In step 818, the computer system 614 computes the electrical properties of the subregions 208–216 of the sample 204 that result in additional, or enhanced, information being generated for those electrical properties. Step 818 is described in greater detail below. When the electrical properties are computed, the computer system 614 proceeds to step 820, thereby completing its processing.

The final measurements of dielectric constant and conductivity electrical properties of a sample 204 can be used in various ways. In the preferred embodiment, the final measurements are used to indicate whether certain tissue in a sample 204 is living or dead, or whether the tissue has a pathology such as clogged arteries and veins, or a cancerous tumor. This information may be presented to a user either in a numerical or enumerated format, a graphical format, or a combination of both. It would be readily apparent to one of ordinary skill in the art to display the final measurements in such a format.

Figure 9:
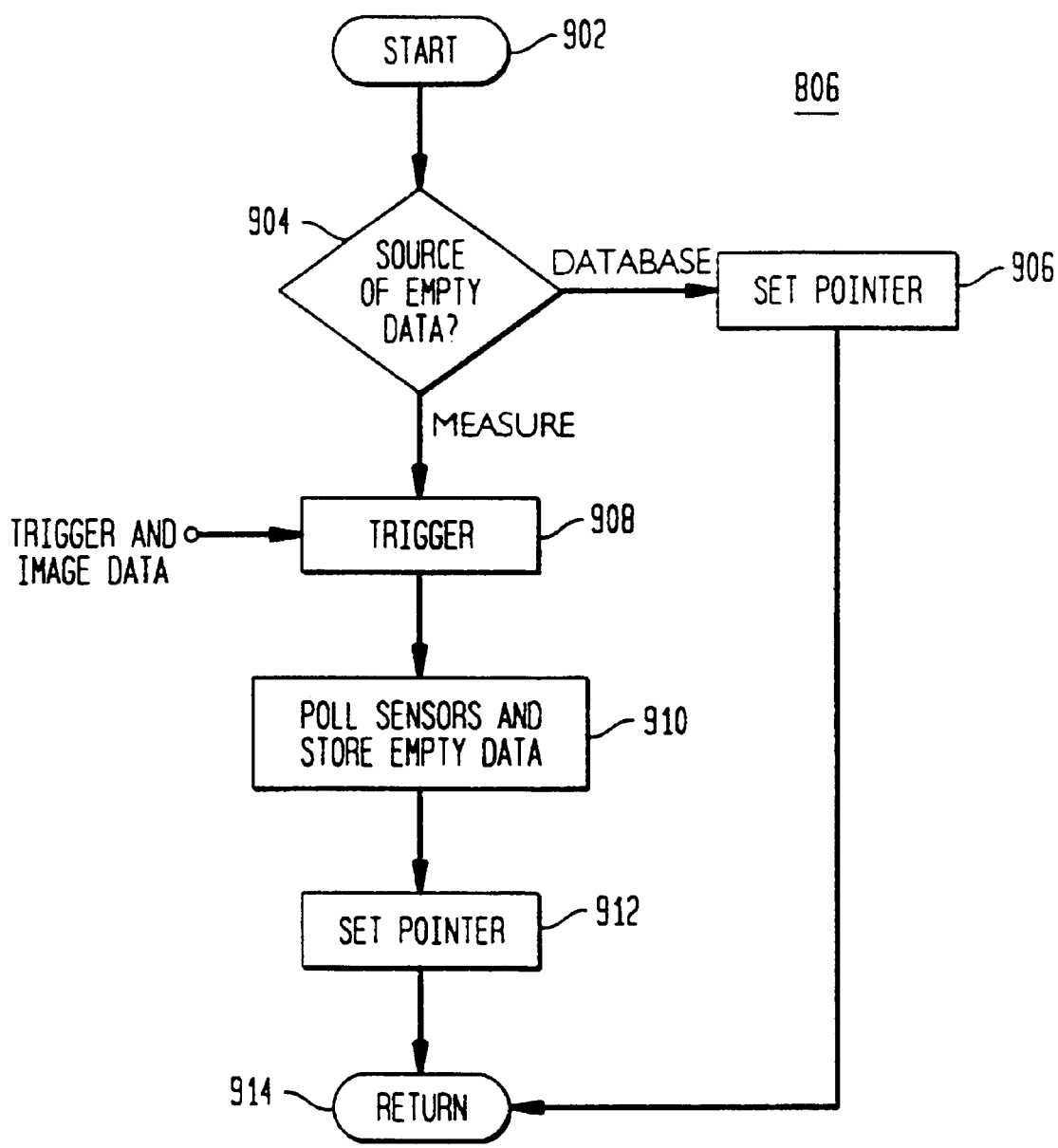
FIG. 9 is a control flow diagram showing the setting of an address pointer for empty data.

FIG. 9 is a block diagram illustrating the processing of step 806 which sets the data pointer for empty data. In step 806, processing begins at step 902 and immediately proceeds to step 904. In step 904, the computer system 614 determines the source of the values to use for an empty sample. If stored data values from a database are to be used, the computer system 614 proceeds to step 906. In step 906, the computer system 614 sets a pointer to the data location of the empty data according to the appropriate database values and continues to step 914, thereby returning to FIG. 8 and step 808.

Referring again to step 904, if the computer system 614 determines that it must measure the empty data, the computer system 614 proceeds to step 908. In step 908, the computer system 614 waits for a trigger. Concurrent with the previous steps of the EPET apparatus 600, a tomographic device optionally makes a preliminary image of the empty sample holder 500 and transmits this imaging data to the computer system 614 of the EPET apparatus 600, thereby triggering the EPET apparatus 600 to continue its processing to step 910. It is important to note that the tomographic device need not make an image of an empty sample holder 500, but by doing so allows for the checking of the data.

In step 910, the computer system 614 commands the phase sensitive detectors 712, 714 of the controller units 606a–f to poll their sensors and measure the net total charges Q on the segmented sensor plates 606. Once the data is received, the EPET apparatus 600 stores this empty data and continues to step 912. In step 912, the computer system 614 sets a data pointer to the address location for the empty data and proceeds to step 914, thereby returning to FIG. 8 and step 808.

Figure 10:
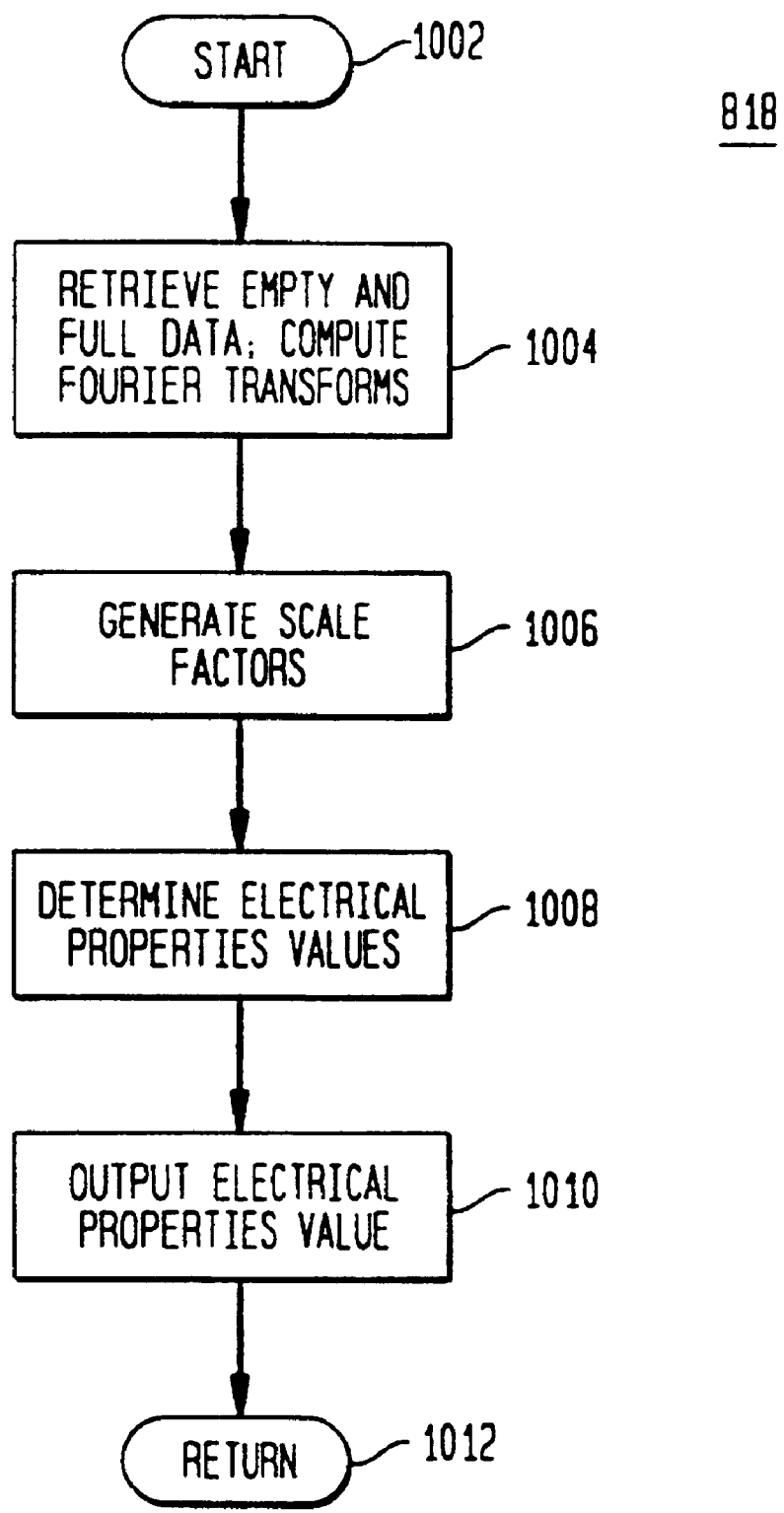
FIG. 10 is a control flow diagram showing the generation of final measurements of electrical properties using the scale factor method.
Figure 11:
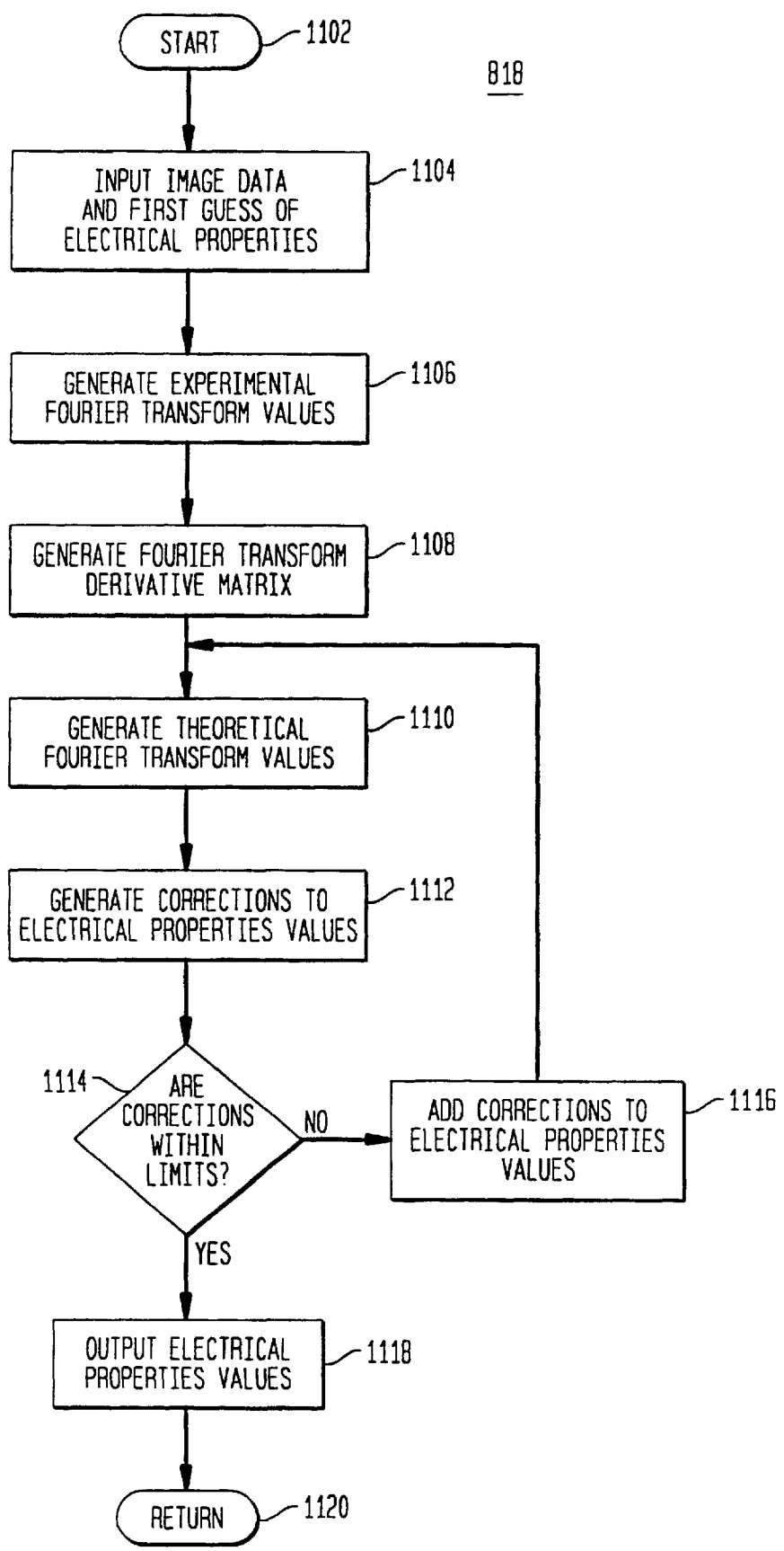
FIG. 11 is a control flow diagram showing the generation of final measurements of electrical properties using the iterative correction method.

Referring again to step 818, there are two different methods by which the computer system 914 of the EPET apparatus 600 of the present invention can compute the electrical properties of a sample 204: the scale factor method and the iterative correction method. FIG. 10 is a block diagram illustrating the operation of the EPET apparatus 600 using the scale factor method for the computations of step 818. Processing begins in step 1002 and immediately proceeds to step 1004. In step 1004, the computer system 614 retrieves the empty and full data and computes the Fourier transform values for both sets of data. The computer system 614 then calculates the difference between the two sets of Fourier transform values. Processing continues to step 1006.

In step 1006, the computer system 614 uses single value decomposition (SVD) to invert the Fourier transform values. SVD is well known in the relevant art and it would be readily apparent to one of ordinary skill in the relevant art to use this mathematical technique. Then, the computer system 614 uses the resulting matrix and determines the scale factor for each of the Fourier values. Proceeding to step 1008, the computer system 614 uses neural net analysis or a look-up table to determine the electrical properties for the sample 204 that correspond to the scale factors. Processing continues to step 1010 wherein the computer system 614 outputs the electrical properties values, e.g., the dielectric constant and conductivity values. The computer system 614 continues to step 1012 and returns to step 820 in FIG. 8, thereby completing all processing.

Referring again to step 818, FIG. 11 illustrates the operation of the EPET apparatus 600 using the iterative correction method for the computing the electrical properties of the sample 204. Processing begins in step 1102 and immediately proceeds to step 1104. In step 1104, the computer system 614 inputs the imaging data from the tomographic device along with the first guess of the electrical properties values, e.g., the dielectric constant and conductivity properties values, for each subregion 208–216 of the sample 204. These first guess electrical properties values are obtained from a known set of such values according to the imaging data. Processing proceeds to step 1106.

In step 1106, the computer system 614 uses the difference between the full and empty data values, called an experimental net total charge Q, to generate an experimental set of Fourier transform values for the net total charges Q. Processing then proceeds to step 1108.

In step 1108, the computer system 614 generates a Fourier transform derivative matrix by using the finite difference and the image data to compute changes in the Fourier transform for a set of assumed changes in each of the dielectric constant and conductivity parameters for each of the subregions 208–216 of the sample 204. Processing proceeds to step 1110 wherein the iterative part of the processing commences.

In step 1110, the computer system 614 uses the finite difference of the guess dielectric constant and conductivity properties values and the image data to compute a theoretical set of Fourier transform values for various values of the index i. The computer system 614 computes these theoretical values for both the in-phase and out-of-phase charge components. Processing proceeds to step 1112.

In step 1112, the computer system 614 calculates a change in the Fourier transform by subtracting the theoretical set of Fourier transform values from the experimental Fourier transform values. The net result is then inverted using single value decomposition and the derivative matrix to obtain the changes, or corrections, in the dielectric constant and conductivity properties values necessary to bring the solution to zero. Processing continues to step 1114.

In step 1114, the computer system 614 determines whether the corrections for the estimated dielectric constant and conductivity properties values are within an acceptable limit. In the preferred embodiment, the acceptable limit is a very small fraction of a percent, e.g., $\frac{1}{100}$th or $\frac{1}{1000}$th. If the computer system 614 determines that the acceptable limit has not been reached, processing continues to step 1116.

In step 1116, the computer system 614 calculates a new set of guess dielectric constant and conductivity properties values by adding the corrections to the previous set of guess electrical properties values. Processing then returns to step 1110 to calculate a new set of theoretical Fourier transform values using these new guesses for the electrical properties values.

Referring again to step 1114, if the computer system 614 determines that the acceptable limit has been reached, processing continues to step 1118 wherein the computer system 614 outputs the electrical properties, the dielectric constant and conductivity, of the sample 204. Proceeding to step 1120, the computer system 614 returns to FIG. 8 at step 820 wherein the processing is complete.

In the preferred embodiment of the EPET apparatus 600 and its operation, it was found that a stability "noise", related to changes in the electrical properties of the sample 204 or movement of the sample 204 during measurement of the charges, of approximately 1%, or a noise of approximately ¹/₁₀th of a percent of full-scale measurement of the charges (electronic measurement noise) leads to an accuracy in the final measurements of the dielectric constant and conductivity values throughout the entire sample 204 of much better than one percent. This is true when the charge detected by the phase sensitive detectors 604, 616 measurement is averaged over 200 cycles of the measuring frequency, i.e., the phase sensitive detector time constant is 200 measurement cycles, e.g., 20 microseconds for a 10 Megahertz measuring frequency. This combination of measuring limits and final accuracy of the measurement (better than 1% accuracy for stability of 1% and full scale charge measuring accuracy of 0.1% during a very fast measuring scheme of 200 cycles of the measuring frequency) is extremely good. Therefore, it is possible to measure the electrical properties of humans, where body motions and fluid changes will occur in times of 0.1 to 1 seconds, essentially instantaneously. The most accurate measurements of this type so far reported using conventional electrical property imaging techniques yield results with 10% to 40% accuracy. The accuracies achieved by the present invention allow for the possible realization of the tremendous diagnostic value of impedance tomography.

Figure 12:
FIG. 12 is an original CAT scan of a human male pelvis.

5. Experimental Results using the EPET Apparatus and Method of the Present Invention An experiment using the EPET apparatus and method of the present invention was executed on a pelvic cross section of a male subject. The initial data on the pelvic cross section is obtained from a CAT scan on a live subject, as shown in FIG. 12.

Figure 13:
FIG. 13 is a first estimate of the identification of various tissue types in the original CAT scan of a human male pelvis.
Figure 14:
FIG. 14 is a smoothed identification of the various tissue types identified in the original CAT scan of a human male pelvis.
Figure 15:
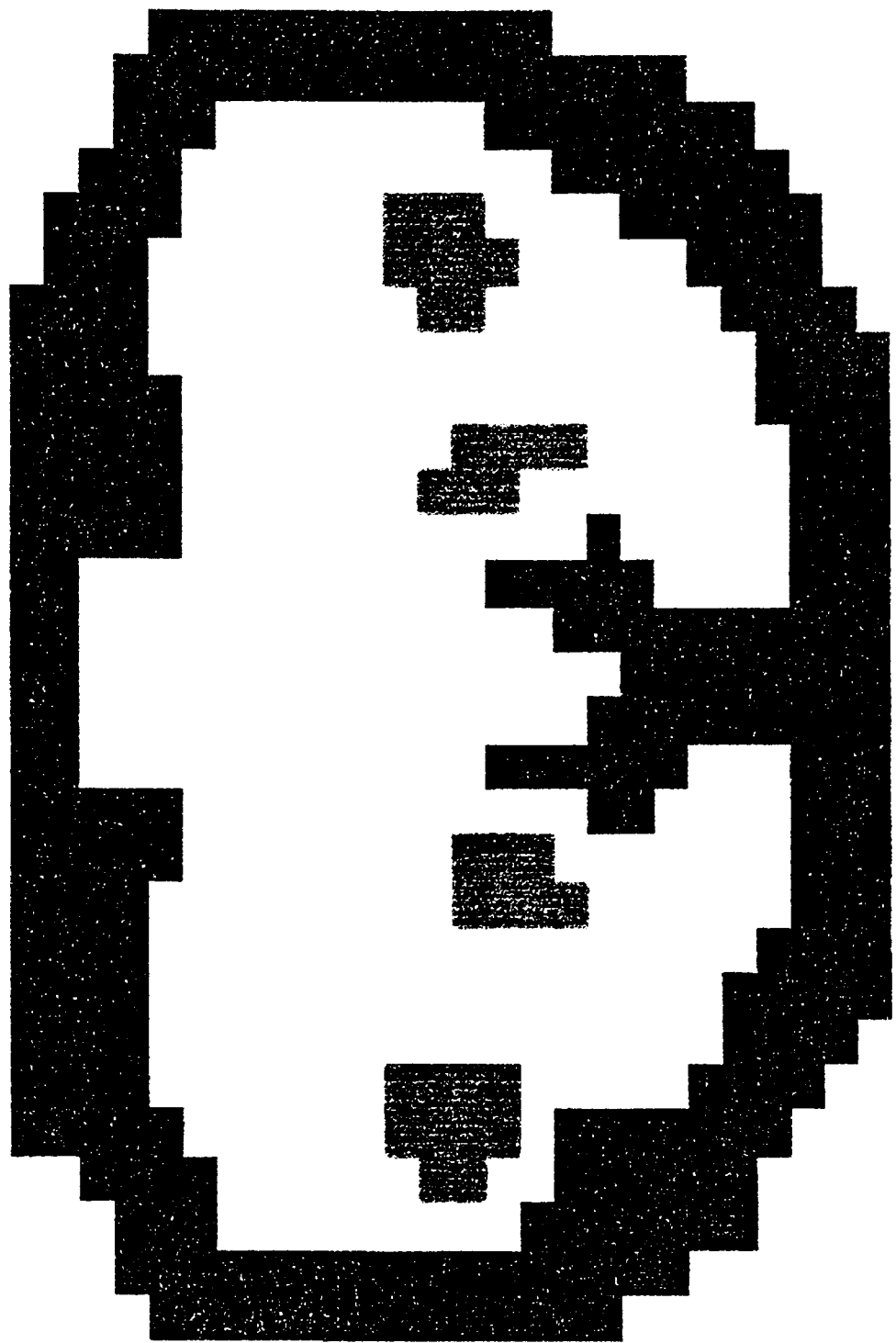
FIG. 15 is a a 30×200 pixel finite difference of the various tissue types identified in the original CAT scan of a human male pelvis.

The first step was to convert the CAT scan data to first dielectric constant and conductivity properties value estimates. That is, the subregions of material in the pelvic were identified to each tissue type. A certain intensity of x-ray was associated with each tissue type as a first estimate. See FIG. 13. These first estimates for the tissue types were then averaged over nearby subregions to smooth out and fill in some of the empty holes. The result is shown in FIG. 14. Finally, this was reduced to a more coarse grid to correspond to the 200×30 grid representing the closed volume space shown in FIG. 5. FIG. 14 is a block diagram showing this coarse grid. Although it appears that the crude grid is too crude for the calculations of the present invention, it is important to note that the increasing number of pixels will not increase the difficulty of the inversion method simply because the number of items to be inverted is simply determined by the number of subregions 208–216 of different tissue type multiplied by two. In fact, the spatial resolution comes primarily from the CAT scan tomographic techniques so that increasing the number of pixels merely helps to identify smaller subregions 208–216 in the image and will reach a final limitation depending on how accurate the inversion can be.

The experiment was conducted using a frequency of $10^7$ Hz. This frequency was used because it represents a point for which there are both sizable dielectric constant and conductivity contributions. The present invention is described with this frequency for convenience purpose only. It would be readily apparent to one of ordinary skill in the relevant art to use a different frequency.

The following data represents a typical page in the simulation output of the present invention as used on a sample of a male pelvis, at 1e7 Hz, Error in the Sample (ERS)=1%, Error in the Circuitry (ERC)=0.01%:

Difference to "Exp."–Real Part (in %):

| Iteration | Skin | Fat | Muscle | Bone |
|---|---|---|---|---|
| 0 | 3.3824 | 3.8783 | 1.3598 | −39.679 |
| 1 | −0.17842 | −0.15289 | 0.10873 | 3.8638 |
| 2 | −0.012763 | −0.0034117 | 0.012589 | −0.81841 |
| 3 | −0.022662 | −0.0072119 | 0.020340 | −0.77095 |
| 4 | −0.022082 | −0.0071552 | 0.019699 | −0.77176 |
| 5 | −0.022116 | −0.0071517 | 0.019747 | −0.77180 |
| 6 | −0.022114 | −0.0071522 | 0.019744 | −0.77179 |
| 7 | −0.022114 | −0.0071522 | 0.019744 | −0.77179 |

Difference to "Exp." –Imaginary Part (in %):

| Iteration | Skin | Fat | Muscle | Bone |
|---|---|---|---|---|
| 0 | −0.89130 | 6.7368 | −1.0363 | −19.169 |
| 1 | 0.11612 | −0.015454 | 0.57884 | 2.7992 |
| 2 | −0.019397 | −0.0012629 | −0.12625 | 0.39991 |
| 3 | −0.0091662 | −0.0012765 | −0.11993 | 0.32970 |
| 4 | −0.0096804 | −0.0013125 | −0.11906 | 0.33083 |
| 5 | −0.0096535 | −0.0013076 | −0.11916 | 0.33080 |
| 6 | −0.0096549 | −0.0013081 | −0.11915 | 0.33080 |
| 7 | −0.0096548 | −0.0013080 | −0.11915 | 0.33080 |

Root Mean Square (RMS) Error:

| Iteration | Total (in %) |
|---|---|
| 0 | 3.3322247 |
| 1 | 0.28851781 |
| 2 | 0.055318098 |
| 3 | 0.054763561 |
| 4 | 0.054574542 |
| 5 | 0.054593542 |
| 6 | 0.054592044 |
| 7 | 0.054592150 |

Regarding the above simulation output, the experimental dielectric constant is the assumed experimental real and imaginary values for each of the tissue types in the sequences shown at the top of each column. The real part is the conductivity and the imaginary part is the angular frequency omega times omega zero times the relative dielectric constant. The "W" values are diagonal matrix elements that appear in the singular value decomposition technique that were used to produce the inversions. These values are generally within two to three orders of magnitude of each other which indicates a well conditioned inverse.

At the bottom of the right hand columns, the assumed values for the errors are found; that is, the circuit error (ERC) of 0.01 percent and a sample error (ERS) of 1 percent. The ERC of 0.01 percent simply means that the tomographic device can measure charges to 0.01 percent full scale. The ERS of 1 percent for the sample 204 implies that the sample 204 remains fixed in position and fixed in dielectric values due to the flow of blood or breathing to within one percent during the period of the measurement. For example, 200 measuring cycles of at least 10 kilohertz results in a 20 millisecond measuring time and at 10 million hertz results in a 20 microsecond measuring time. Even the value at 10 kilohertz is quite acceptable and within the present range of measurement It would be in fact quite likely that during that period of time the sample 204 remains steady, the ERS is approximately one percent and can even achieve an error rate of much better than one percent.

The Root Mean Square (RMS) table shows the results of applying the iterative correction method. The results are expressed as a percentage between the trial value at any iteration and the so called true or experimental value. This is done for both the real and imaginary parts of the electrical properties and for the RMS total error between the two. This RMS total error can be viewed essentially as the size of the vector connecting the true dielectric vector and the best guess dielectric vector in terms of the averaging magnitude of either one of them or the average magnitude of the true or experimental value.

It is important to note that in approximately three iterations, there is very little change afterwards in that the total error for the assumed input errors is only 0.05 percent. In terms of the individual components, there is an error as small as 0.001 percent and as large as 0.77 percent. Typically, the error over all is much smaller than the average sample error (ERS) going in and the error for any one component is generally smaller than the sample error.

Conclusion

While various embodiments of the present invention have been described above, it should be understood that they have been presented by way of example only, and not limitation. It will be understood by those skilled in the art that various changes in form and details may be made therein without departing from the spirit and scope of the invention as defined in the appended claims. Thus, the breadth and scope of the present invention should not be limited by any of the above-described exemplary embodiments, but should be defined only in accordance with the following claims and their equivalents.

What is claimed is:

1. A method for providing enhanced information of the electrical properties of a sample measured with a tomographic device and an electrical property enhanced tomography (EPET) apparatus, comprising the steps of:

(a) generating an electromagnetic field in a sample holder by applying frequency dependent voltages of predetermined amplitude to an array of sensors that form a surface to be placed in electrical connection with the sample, such that time dependent net total electric charges are produced on the surface of the sample holder;

(b) determining the time dependent net total electric charges on the surface of the sample holder, wherein the sample holder is filled with a matching medium and the sample is not in the sample holder, thereby generating empty data values;

(c) inserting the sample into the sample holder wherein the matching medium is disposed between the sample and the sample holder to provide electrical connection between the sample and the sensors;

(d) inputting initial image data of the sample from the tomographic device;

(e) determining the time dependent net total electric charges on the surface of the sample holder when the sample is within the sample holder, thereby generating full data values;

(f) generating from said empty data values, said initial image data and said full data values enhanced information on the electrical properties of the sample; and (g) outputting said enhanced information.

2. The method according to claim 1, wherein said step (f) uses the scale factor method, comprising the steps of:

(f)(1) generating first Fourier transform values 1004 for said empty data values;

(f)(2) generating second Fourier transform values 1004 for said full data values;

(f)(3) computing the difference 1004 between said second Fourier transform values and said first Fourier transform values, thereby generating third Fourier transform values;

(f)(4) inverting said third Fourier transform values 1004, thereby generating inverted Fourier transform values;

(f)(5) determining scale factors 1006 for said inverted Fourier transform values; and (f)(6) generating enhanced information 1008 of the electrical properties of the sample 204 based on said scale factors.

3. The method according to claim 2, wherein said step (f)(4) uses singular value decomposition.

4. The method according to claim 2, wherein said step (f)(6) uses neural network analysis.

5. The method according to claim 2, wherein said step (f)(6) uses a look up table.

6. The method according to claim 1, wherein said step (f) uses the iterative correction method, comprising the steps of:

(f)(1) inputting 1104 image data on the sample 204 and a guess of the electrical properties values of the sample 204;

(f)(2) generating experimental Fourier transform values 1106;

(f)(3) generating a Fourier transform derivative matrix 1108;

(f)(4) generating theoretical Fourier transform values 1110;

(f)(5) calculating corrections 1112 to said guess of the electrical properties values of the sample 204, (f)(6) determining whether said corrections are within an acceptable limit 1114; and (f)(7) generating a new guess of the electrical properties values 116 of the sample 204 by adding said corrections to said guess electrical properties and returning to step (f)(4), if it is determined in step (f)(6) that said corrections are not within said acceptable limit.

7. The method according to claim 1, further comprising the step of:

(h) triggering said step (e) upon the completion of said step (d).

8. The method according to claim 1, further comprising the step of:

(h) triggering said step (e) when noise associated with the sample 204 is minimized.

9. The method according to claim 8, wherein the sample 204 is a human subject and said triggering of said step (h) occurs at an appropriate cardiac cycle of the human subject.

10. The method according to claim 8, wherein the sample 204 is a human subject and said triggering of said step (h) occurs at an appropriate pulmonary cycle of the human subject.

11. A computer program product for use with a computer system of an Electrical Property Enhanced Tomography (EPET) apparatus for providing information of the electrical properties of a sample being measured with a tomographic device, which comprises:

a computer usable medium having computer readable program code means embodied in said medium for generating object code for a computer, said computer readable program code means having:

a first computer readable program code means for operating the computer system to control an electromagnetic field in a sample holder by applying frequency dependent voltages of predetermined amplitude to an array of sensors that form a surface to be placed in electrical connection with the sample, such that time dependent net total electric charges are produced on the surface of the sample holder;

a second computer readable program code means for operating the computer system to determine the time dependent net total electric charges on the surface of the sample holder while the sample is not present in the sample holder to thereby generate empty data values;

a third computer readable program code means for operating the computer system to input initial Image data from the tomographic device when the sample is placed in the sample holder;

a fourth computer readable program code means for operating the computer system to determine the time dependent net total electrical charges on the surface of the sample holder when the sample is within the sample holder, thereby generating full data values;

a fifth computer readable program code means for operating the computer system in response to the generated empty data values, the received initial image data, and the generated full data values to produce enhanced information on the electrical properties of the sample; and a sixth computer readable program code means for operating the computer system to output said enhanced information on the electrical properties of the sample.

12. The computer program product according to claim 11, wherein said fifth computer readable program code means, comprises:

a means for generating first Fourier transform values 1004 for said empty data values;

a means for generating second Fourier transform values 1004 for said full data values;

a means for computing the difference 1004 between said second Fourier transform values and said first Fourier transform values, thereby generating third Fourier transform values;

a means for inverting said third Fourier transform values 1004, thereby generating inverted Fourier transform values;

a means for determining scale factors 1006 for said inverted Fourier transform values; and a means for generating said enhanced information 1008 of the electrical properties of the sample 204 based on said scale factors.

13. The computer program product according to claim 12, wherein said means for inverting uses singular value decomposition.

14. The computer program product according to claim 12, wherein said means for generating said enhanced information 1008 uses neural network analysis.

15. The computer program product according to claim 12, wherein said means for generating said enhanced information 1008 uses a look up table.

16. The computer program product according to claim 11, wherein said means for inverting uses the iterative correction method, comprising the steps of:

a means for inputting 1104 image data on the sample 204 and a guess of the electrical properties values of the sample 204;

a means for generating experimental Fourier transform values 1106;

a means for generating a Fourier transform derivative matrix 1108;

a means for generating theoretical Fourier transform values 1110;

a means for calculating corrections 1112 to said guess of the electrical properties values of the sample 204;

a means for determining whether said corrections are within an acceptable limit 1114; and a means for generating a new guess of the electrical properties values 1116 of the sample 204 by adding said corrections to said guess electrical properties and returning to said means for generating theoretical Fourier transform values 1110, if it is determined by said means for determining whether said corrections are within said acceptable limit 1114 that said corrections are not within said acceptable limit.

17. The computer program product according to claim 11, further comprising:

a means for triggering said fourth computer readable program code means upon the completion of said third computer readable program code means.

18. The computer program product according to claim 11, further comprising:

a means for triggering said fourth computer readable program code means when noise associated with the sample 202 is minimized.

19. The computer program product according to claim 11, wherein said second computer readable program code means and said fourth computer readable program code means detects an instantaneous value of a time dependent net total electric charge.

20. The computer program product according to claim 11, wherein said second computer readable program code means and said fourth computer readable program code means detects a net total electrical current produced by the flow of a time dependent net total electric charge.

21. A method for producing an image indicative of an electrical characteristic of an object, the steps comprising:

a) applying a voltage to the surface of the object with an array of sensor elements that make electrical connection with the surface;

b) measuring the surface charge at each sensor element that results from the applied voltage;

c) transforming the surface charge measurements;

d) calculating from the transformed surface charge measurements and image data input from a tomographic device electrical characteristic values throughout the object; and e) producing an image of the electrical characteristic of the object from said calculated electrical characteristic values.

22. The method as recited in claim 21 in which the array of sensor elements includes a first set of sensor elements disposed on one side of the object and a second set of sensor elements disposed on the other side of the object, and step a) is performed by applying the voltage across said first and second set of sensor elements.

23. The method as recited in claim 22 in which the surface charge is measured at each sensor element by measuring the current flowing therethrough.

24. The method as recited in claim 22 which includes:

f) repeating steps a), b), and c) without the object being disposed between the first and second set of sensor elements; and step d) includes: computing difference transformed values by subtracting the transformed surface charge measurements made with the object disposed between the first and second set of sensor elements and the transformed surface charge measurements made without the object disposed between the first and second set of sensor elements.

25. The method as recited in claim 24 in which step d) further includes:

inverting the difference transformed values to thereby produce inverted transformed values; and determining scale factors for said inverted transformed values.

26. The method as recited in claim 25 in which the electrical characteristic values are calculated in step d) using a neural network analysis.

27. The method as recited in claim 25 in which the electrical characteristic values are calculated in step d) using a look up table.

28. The method as recited in claim 21 which includes inserting an impedance matching media between the sensor elements and the surface of the object to make electrical connection therebetween.

29. The method as recited in claim 21 in which the image produced in step e) indicates the electrical conductivity throughout the object.

30. The method as recited in claim 21 in which the image produced in step e) indicates the dielectric constant throughout the object.

31. The method as recited in claim 21 in which the image produced in step e) is produced by setting the intensity of each pixel in the image to a level corresponding to the value of the electrical property at the corresponding location in the object.

32. The method as recited in claim 21 in which the transformation performed in step c) is a Fourier transformation.

33. An imaging system for producing an image indicative of an electrical property of an object which comprises:

an array of sensor elements for placement in electrical connection with the surface of the object;

means for applying a predetermined voltage to the array of sensor elements;

means for measuring the electrical charge at each of the sensor elements while the voltage is applied;

means for transforming the measured electrical charges to a set of transformed surface charges;

means responsive to image data input from a tomographic device for calculating electrical characteristic values at locations throughout the object from the set of transformed surface charges; and means for producing an image depicting the electrical characteristic throughout the object from the calculated electrical characteristic values.

34. The imaging system as recited in claim 33 in which the array of sensor elements includes a top array disposed on one side of the object and a bottom array disposed on the opposite side of the object.

35. The imaging system as recited in claim 34 which includes a matching medium disposed between each of the top and bottom arrays and the object to make electrical connection therebetween.

36. The imaging system as recited in claim 35 in which the impedance of the matching medium is substantially the same as that of the object being imaged.

37. The imaging system as recited in claim 34 in which each of the top and bottom arrays includes a segmented sensor plate, the means for applying a voltage includes means for controlling the voltage amplitude and frequency to each segment, and the means for measuring the electrical charge includes means for detecting the time dependent net total electric charges at each of said segments.

38. The imaging system as recited in claim 37 in which the means for detecting the time dependent net total electric charge includes means for detecting a net total electric current flowing through its associated segment.

39. The imaging system as recited in claim 34 in which the array of sensor elements also includes a pair of spaced side arrays disposed on opposite sides of the object and positioned with respect to the top and bottom arrays to substantially surround the object.

40. The imaging system as recited in claim 33 in which the means for applying a voltage includes a frequency source for applying an alternating voltage at a selected frequency to the array of sensor elements.

41. The imaging system as recited in claim 33 in which the object is a living animal and means for producing a trigger signal responsive to physiological motion in the living animal is coupled to the means for measuring the electrical charge to initiate said measurement.

42. The imaging system as recited in claim 33 in which the array of sensor elements encircles the object.

43. The imaging system as recited in claim 42 in which the array of sensor elements has a fixed geometric shape and a matching medium is disposed between the array of sensor elements and the object to make electric connection therebetween.

44. The imaging system as recited in claim 43 in which the means for measuring the electrical charge includes a plurality of controller units which enable the electrical charge to be measured on all of the sensor elements at substantially the same time.

45. The imaging system as recited in claim 33 in which the means for measuring the electrical charge includes a plurality of controller units which enable the electrical charge to be measured on all of the sensor elements at substantially the same time.

* * * * *